(12) United States Patent  
Hoar et al.

(10) Patent No.: US 12,046,370 B2  
(45) Date of Patent: Jul. 23, 2024

(54) INTEGRATED DISEASE MANAGEMENT SYSTEM

(71) Applicant: Embecta Corp., Andover, MA (US)

(72) Inventors: Michael Hoar, Westford, MA (US); Douglas McClure, Framingham, MA (US); Rita Saltiel-Berzin, Ramsey, NY (US); Edward Liebowitz, Jersey City, NJ (US)

(73) Assignee: Embecta Corp., Andover, MA (US)

( * ) Notice: Subject to any disclaimer, the term of this patent is extended or adjusted under 35 U.S.C. 154(b) by 173 days.

(21) Appl. No.: 17/750,984

(22) Filed: May 23, 2022

(65) Prior Publication Data

US 2023/0008055 A1 Jan. 12, 2023

Related U.S. Application Data

(63) Continuation of application No. 16/340,980, filed as application No. PCT/US2017/056196 on Oct. 11, 2017, now Pat. No. 11,367,532.

(Continued)

(51) Int. Cl.
*G16H 50/20* (2018.01)
*A61B 5/00* (2006.01)
(Continued)

(52) U.S. Cl.
CPC .......... *G16H 50/20* (2018.01); *A61B 5/0205* (2013.01); *A61B 5/14532* (2013.01);
(Continued)

(58) Field of Classification Search
CPC ........ G16H 50/20; G16H 10/60; G16H 20/30; G16H 20/60; G16H 20/70; G16H 20/10;
(Continued)

(56) References Cited

U.S. PATENT DOCUMENTS 6,629,937 B2   10/2003  Watrous
6,855,556 B2    2/2005  Amiss et al.
(Continued)

FOREIGN PATENT DOCUMENTS

CN   101739510 A   6/2010
CN   204613944 U   9/2015
(Continued)

OTHER PUBLICATIONS

Hoshino, Atsushi, "An Integrated Conversation Robot Interface for Task-Oriented and Non-Task-Oriented Dialogues", FIT 2006, 5th Forum on Information Technology, Japan, The Institute of Electronics, Information and Communication Engineers, Aug. 21, 2006, pp. 127-128.

(Continued)

*Primary Examiner* — Omar Casillashernandez
(74) *Attorney, Agent, or Firm* — Greenberg Traurig, LLP; David J. Dykeman; Roman Fayerberg

(57) ABSTRACT

An integrated disease management system provides patients with simple, quick, and readily available counseling regarding a healthy diabetic lifestyle. The system can include an interactive engine with predictive analytics and machine learning to provide a customized experience for a user. The system can be configured to transmit data to a remote server to perform analysis of received data (e.g., disease management data), to provide feedback to the user (e.g., customized feedback with curated content based on a user's data and interface interactions) and send all or a portion of the data and/or curated content to another user device or remote health management access point (e.g., as cloud storage) where the information can be accessed by healthcare stakeholder.

18 Claims, 17 Drawing Sheets

Related U.S. Application Data

(60) Provisional application No. 62/545,889, filed on Aug. 15, 2017, provisional application No. 62/407,367, filed on Oct. 12, 2016.

(51) Int. Cl.
| | |
|---|---|
| *A61B 5/0205* | (2006.01) |
| *A61B 5/145* | (2006.01) |
| *G16H 10/60* | (2018.01) |
| *G16H 20/30* | (2018.01) |
| *G16H 20/60* | (2018.01) |
| *G16H 20/70* | (2018.01) |

(52) U.S. Cl.
CPC .......... *A61B 5/7465* (2013.01); *A61B 5/7475* (2013.01); *G16H 10/60* (2018.01); *G16H 20/30* (2018.01); *G16H 20/60* (2018.01); *G16H 20/70* (2018.01)

(58) Field of Classification Search
CPC ........ G16H 40/63; G16H 40/67; G16H 50/70; G16H 70/20; G16H 70/40; G16H 70/60; G16H 80/00; A61B 5/0205; A61B 5/14532; A61B 5/7465; A61B 5/7475; A61B 5/1459; A61B 5/1455; A61B 5/1495; A61B 5/1118; A61B 2560/0223; A61B 5/6898
USPC .................................................. 340/539.12
See application file for complete search history.

(56) References Cited

U.S. PATENT DOCUMENTS

| | | | |
|---|---|---|---|
| 7,496,392 B2 | 2/2009 | Alarcón et al. | |
| 7,702,524 B1* | 4/2010 | Whibbs | G16H 80/00 |
| | | | 705/2 |
| 7,769,600 B2 | 8/2010 | Iliff | |
| 7,787,923 B2 | 8/2010 | Alarcon et al. | |
| 7,792,561 B2 | 9/2010 | Alarcon et al. | |
| 7,851,593 B2 | 12/2010 | Isieh et al. | |
| 8,094,009 B2 | 1/2012 | Allen et al. | |
| 8,548,828 B1 | 10/2013 | Longmire | |
| 8,566,121 B2 | 10/2013 | Ramasubramanian et al. | |
| 8,623,639 B2 | 1/2014 | Amiss et al. | |
| 8,690,578 B1 | 4/2014 | Nusbaum et al. | |
| 8,930,204 B1 | 1/2015 | Igoe et al. | |
| 9,060,683 B2 | 6/2015 | Tran | |
| 9,081,879 B2 | 7/2015 | Iliff | |
| 9,269,116 B2 | 2/2016 | Bulat | |
| 9,592,742 B1 | 3/2017 | Sosinov et al. | |
| 10,252,058 B1 | 4/2019 | Fuerst | |
| 10,418,863 B1 | 9/2019 | Jadidian et al. | |
| 10,853,455 B2* | 12/2020 | Foster | G16H 40/20 |
| 11,367,532 B2 | 6/2022 | Hoar et al. | |
| 2001/0042119 A1 | 11/2001 | Urano et al. | |
| 2001/0047125 A1 | 11/2001 | Quy | |
| 2003/0046113 A1* | 3/2003 | Johnson | G16H 20/00 |
| | | | 705/3 |
| 2003/0050538 A1* | 3/2003 | Naghavi | G16H 40/67 |
| | | | 600/300 |
| 2003/0061054 A1* | 3/2003 | Payne | G10L 15/26 |
| | | | 704/E15.044 |
| 2003/0092972 A1* | 5/2003 | Mantilla | G16H 40/67 |
| | | | 600/300 |
| 2005/0075970 A1 | 4/2005 | Doyle | |
| 2005/0240444 A1 | 10/2005 | Wooten et al. | |
| 2006/0235280 A1 | 10/2006 | Vonk et al. | |
| 2007/0015971 A1 | 1/2007 | Atignal et al. | |
| 2007/0185390 A1 | 8/2007 | Perkins et al. | |
| 2007/0255115 A1* | 11/2007 | Anglin, Jr. | G16H 10/60 |
| | | | 600/300 |
| 2009/0007924 A1* | 1/2009 | Iliff | G16H 50/20 |
| | | | 600/300 |
| 2009/0183105 A1* | 7/2009 | Teel, IV | G06F 8/60 |
| | | | 715/771 |
| 2010/0174229 A1* | 7/2010 | Hsu | A61M 5/142 |
| | | | 340/5.82 |
| 2010/0256457 A1 | 10/2010 | Schaffer et al. | |
| 2010/0332142 A1* | 12/2010 | Shadforth | A61B 5/4833 |
| | | | 600/300 |
| 2011/0084659 A1 | 4/2011 | Niemann et al. | |
| 2011/0145747 A1* | 6/2011 | Wong | A61B 5/7264 |
| | | | 709/219 |
| 2012/0224057 A1 | 9/2012 | Gill et al. | |
| 2014/0012558 A1 | 1/2014 | Mansi et al. | |
| 2014/0108023 A1 | 4/2014 | Arkoff | |
| 2014/0156308 A1 | 6/2014 | Ohnemus et al. | |
| 2014/0188895 A1 | 7/2014 | Wang et al. | |
| 2014/0280474 A1* | 9/2014 | Lynn | G16H 40/67 |
| | | | 709/203 |
| 2014/0297326 A1* | 10/2014 | Firozvi | G16H 10/60 |
| | | | 705/3 |
| 2014/0330579 A1* | 11/2014 | Cashman | G06Q 10/1095 |
| | | | 705/2 |
| 2015/0216413 A1 | 8/2015 | Soyao et al. | |
| 2015/0227710 A1 | 8/2015 | Pappada | |
| 2016/0321430 A1 | 11/2016 | Eckman et al. | |
| 2017/0056605 A1 | 3/2017 | Kondo et al. | |
| 2017/0220751 A1 | 8/2017 | Davis et al. | |
| 2019/0076604 A1 | 3/2019 | Fiedler et al. | |
| 2019/0160972 A1 | 5/2019 | Zeiler et al. | |
| 2019/0167902 A1* | 6/2019 | Kamen | A61M 5/14244 |
| 2019/0183434 A1 | 6/2019 | Sjolund et al. | |
| 2019/0190306 A1 | 6/2019 | Sosinov et al. | |
| 2019/0237181 A1 | 8/2019 | Steinberg | |
| 2020/0027535 A1 | 1/2020 | Memmelaar et al. | |
| 2020/0030551 A1 | 1/2020 | Bøggild-Damkvist et al. | |
| 2021/0241905 A1 | 8/2021 | Hoar et al. | |

FOREIGN PATENT DOCUMENTS

| | | |
|---|---|---|
| CN | 105718741 A | 6/2016 |
| JP | 2006075593 A | 3/2006 |
| JP | 2008186439 A | 8/2008 |
| KR | 20160043777 A | 4/2016 |
| WO | 2013029032 A1 | 2/2013 |
| WO | 2015089484 A1 | 6/2015 |
| WO | 2018071579 A1 | 4/2018 |
| WO | 2019245987 A1 | 12/2019 |
| WO | 2021168078 A1 | 8/2021 |

OTHER PUBLICATIONS

Office Action dated Sep. 7, 2022 in corresponding Chinese Patent Application No. 201780063056.3 (7 pages).
International Search Report for International Application No. PCT/US17/56196 dated Dec. 22, 2017.
International Search Report for International Application No. PCT/US2019/037526 dated Oct. 11, 2019.
International Search Report for International Application No. PCT/US2021/018529 dated Apr. 28, 2021.
International Search Report for International Application No. PCT/US2021/043529 dated Nov. 4, 2021.
International Search Report and Written Opinion (n.d.) in corresponding International Patent Application No. PCT/US2020/067762 (14 pages).

* cited by examiner

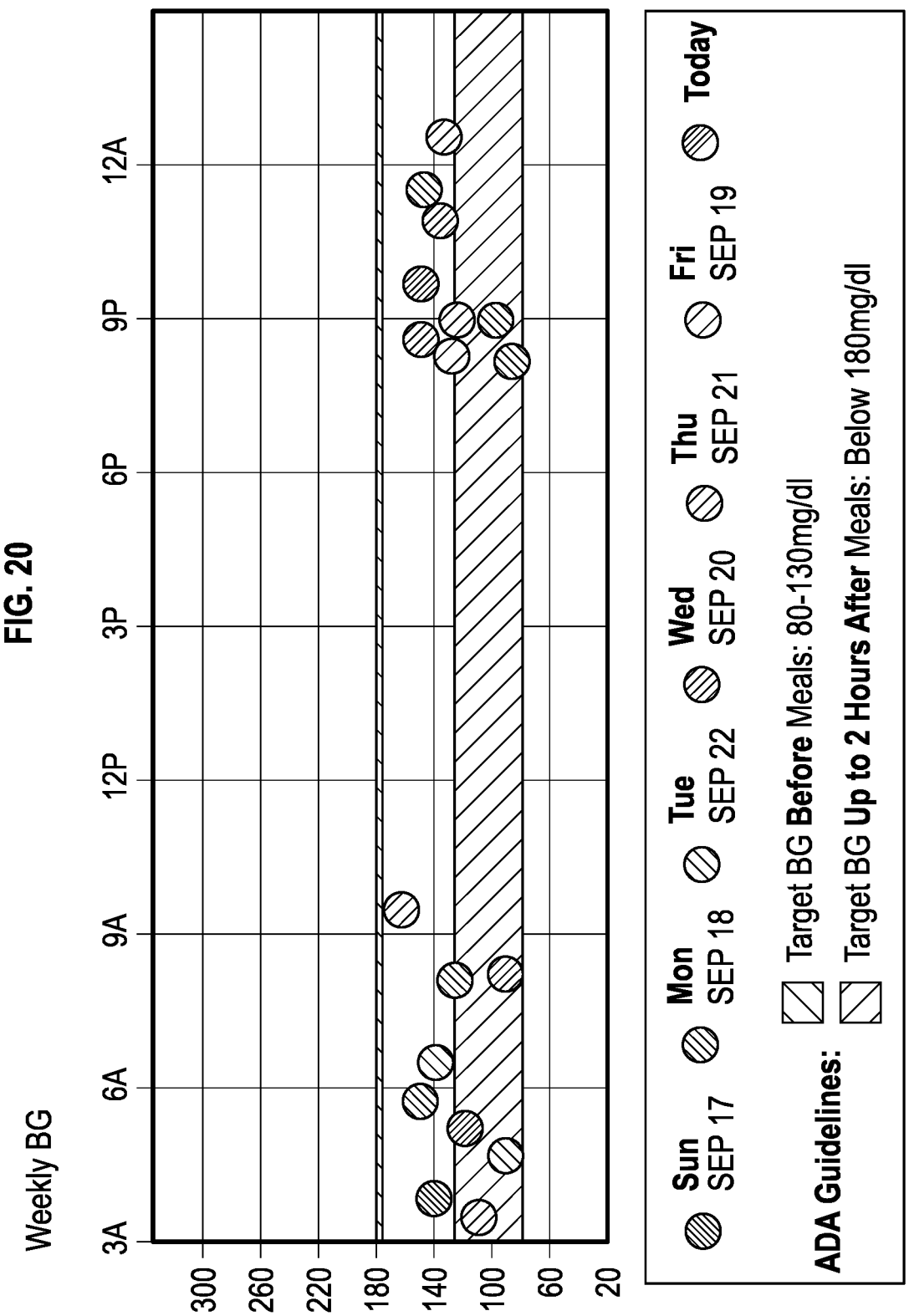

INTEGRATED DISEASE MANAGEMENT SYSTEM

CROSS REFERENCE TO RELATED APPLICATIONS

This application is a continuation application of U.S. application Ser. No. 16/340,980, filed Apr. 10, 2019, which is a U.S. national phase application of PCT International Application No. PCT/US2017/056196, filed Oct. 11, 2017, which claims the benefit of and priority to U.S. Provisional Application No. 62/407,367 filed Oct. 12, 2016, and U.S. Provisional Application No. 62/545,889 filed Aug. 15, 2017. The contents of each of these applications are incorporated herein by reference in their entireties.

BACKGROUND

Field

This disclosure relates to systems and methods for managing illnesses and diseases, and, in particular, to an integrated disease management system that includes a communications interface between a patient and the system that can provide smart, connected, end-to-end solutions for delivering personalized insights to the patient or other users. In a particular example, the integrated disease management system is an integrated diabetes management system.

Description

Diabetes is a group of diseases marked by high levels of blood glucose resulting from defects in insulin production, insulin action, or both. Diabetes can lead to serious complications and premature death. There are, however, well-known products and strategies available to patients with diabetes to help control the disease and lower the risk of complications.

Treatment options for diabetics include, for example, specialized diets, oral medications, and/or insulin therapy. The primary goal of diabetes treatment is to control a diabetic's blood glucose level in order to increase the chance of a complication-free life. Because of the nature of diabetes and its short-term and long-term complications, it is important that diabetics are constantly aware of the level of glucose in their blood and closely monitor their diet. For patients who take insulin therapy, it is important to administer insulin in a manner that maintains glucose levels, and accommodates the tendency of glucose concentration in the blood to fluctuate as a result of meals and other activities.

Healthcare professionals, such as doctors or certified diabetes educators (CDEs), offer counseling to diabetic patients regarding managing diet, exercise, lifestyle, and general health. When followed, this counseling can reduce complications associated with diabetes and allow diabetics to lead healthier and happier lives. Often, however, such counseling is only available by appointment, leaving diabetics without simple, quick, and readily available counseling regarding a healthy diabetic lifestyle.

SUMMARY

Integrated disease management systems and methods are disclosed herein. In certain examples, the disease is diabetes, and the disclosure relates to an integrated diabetes management (IDM) system. The IDM system can provide diabetics with simple, quick, and readily available counseling regarding a healthy diabetic lifestyle.

In one aspect, an IDM system includes an interactive interface. In one non-limiting example, the interactive interface is a chatbot that allows a user to communicate through a chat session to the IDM system. The interactive interface can be available online and accessible via any network connected device. The interactive interface can be accessible via a web browser or an application (such as a mobile phone or computer application). The interactive interface may provide information regarding healthy diabetic lifestyle via interactive prompts and/or responding to questions provided by users. The interactive interface can provide information regarding diet, exercise, and/or general information regarding diabetes, among other the types of information.

In some embodiments, the IDM system stores information about user interactions with the IDM system. The IDM system can use the stored information in future interactions to customize information for the user.

In some embodiments, user health information can be uploaded to the IDM system. User health information can include data entered via the interactive interface, data uploaded from internet-enabled ("smart") devices (such as smart insulin pens or pumps, diabetes monitors, fitness trackers, diet trackers, etc.), among other types of information. The IDM system can analyze the uploaded health information to provide customized information for the user.

The IDM system is designed to allow diabetic patients to feel more in control of their diabetes management, and, in turn, to be in control, leading to better patient outcomes.

Although this disclosure primarily refers to the example of diabetes, the integrated disease management systems and methods described herein can be applied to other illnesses or diseases. This disclosure should not be limited only to application to management of diabetes.

Additional and/or other aspects and advantages of the present invention will be set forth in the description that follows, or will be apparent from the description, or may be learned by practice of the invention. The present invention may comprise and integrated diabetes management system and related devices and software apps and methods for operating same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 20 is an example screen illustrating a weekly visualization of patient data.

DETAILED DESCRIPTION

Introduction

Figure 1:
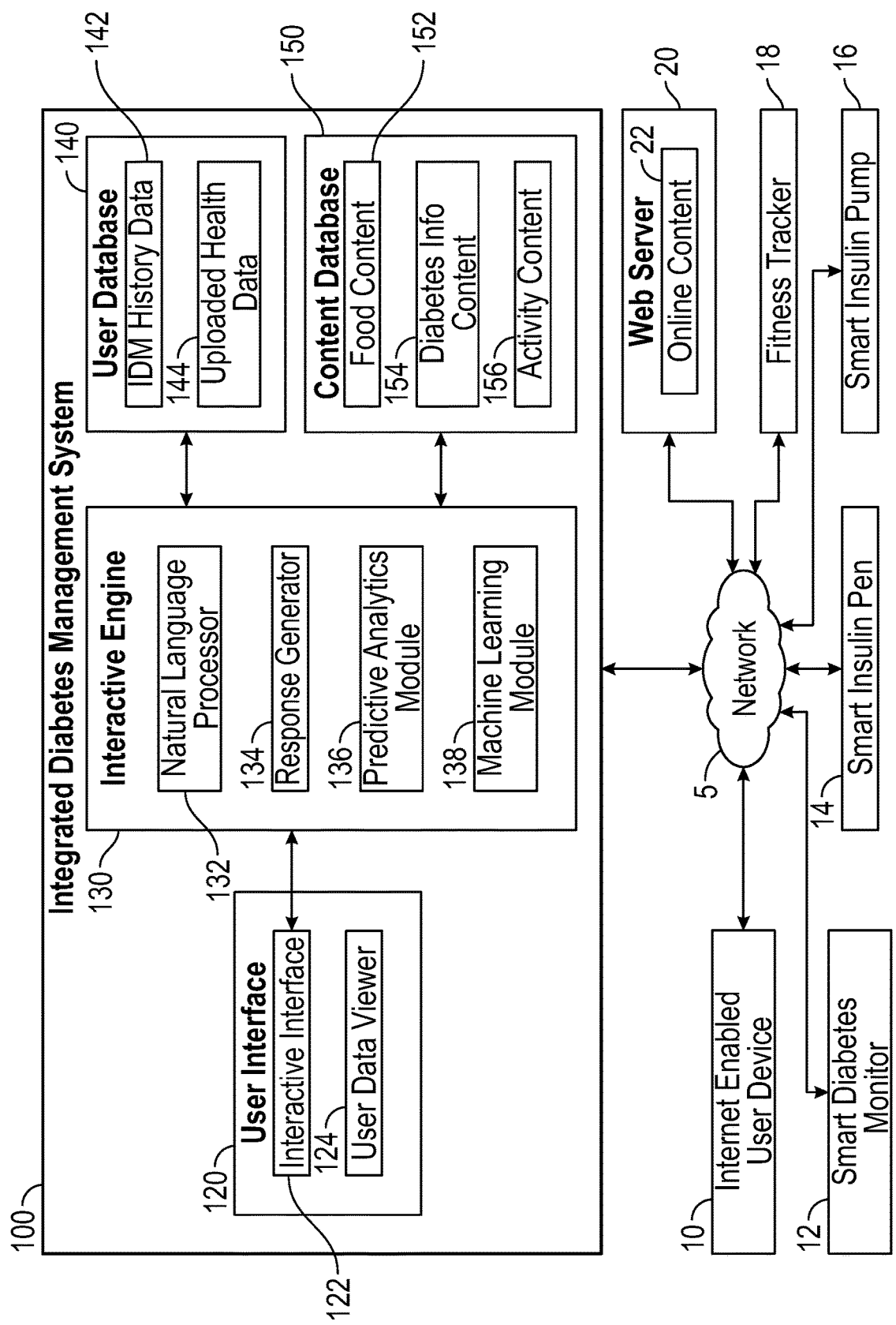
FIG. 1 is a block diagram illustrating an integrated diabetes management (IDM) system according to one embodiment.

This disclosure relates to integrated disease management systems and methods. The integrated disease management systems and methods can include or use an interactive interface (e.g., an automated interactive interface, such as a chatbot) to aid a patient in managing his or her disease or illness. In some embodiments, integrated disease management systems and methods receive information about the user from one or more user devices, such as internet-enabled user devices (e.g., a smartphone) or other smart or connected devices (such as patient monitors, fitness trackers, etc.). The information received from these devices can be used to customize the integrated disease management systems and methods for the user, providing an efficient and effective means for managing the illness or disease. In certain embodiments, the illness or disease is diabetes.

One aspect of effective diabetes management is education that facilitates changes in behavior to help improve glucose control and other health outcomes. Unfortunately, many diabetic patients often receive minimal instructional information, if any at all, about how to manage their diabetes. Further, in many instances, such instructional information is only available by appointment with healthcare professionals, such as doctors or CDEs. To maximize success, diabetic patients need ongoing reinforcement of key concepts and behaviors, as well as ready access to information about diabetes. Without this ongoing reinforcement and readily available information, therapy adherence has been shown to decline, healthy living behaviors stop, and diabetes-related complications increase, leading to expensive care and interventions, as well as decreased quality of life.

In addition to lacking accessible lifestyle training, diabetics also lack convenient means to record their diabetes management data (e.g., blood glucose readings and insulin intake) and also lack comprehensive use of their diabetes management data. As stated above, treatment options for people with diabetes include specialized diets, oral medications and/or insulin therapy. A need exists for improved diabetes therapy which could include continuous monitoring of blood glucose levels, and data capture for insulin dosing, dietary intake (e.g., carbohydrate estimation), activity tracking, stress levels, and other factors. By continuously monitoring numerous factors important for diabetes management, healthcare professionals can maximize the effectiveness of the treatment regimen for each patient. Unfortunately, conventional diabetes treatment regimens, including multiple daily injections (MDI), insulin pens, patch pumps and insulin pumps, do not provide means to adequately record information on medication doses delivered to the patient or other diabetes management information such as glucose levels, level of activity, or carbohydrate intake to provide feedback to the patient and their member of their care team.

To properly diagnose and treat diabetes, the patient and/or Health Care Provider (HCP) needs to evaluate at least the short-term, daily records for (1) insulin dosing, (2) oral medications, (3) blood glucose measurement (BGM), and (4) carbohydrate intake. These data are obtained from various sources, such as the setting on an insulin pen, the episodic reading from a BGM meter, and the estimate of carbohydrates in a meal, all determined and typically transposed by the patient into a logbook or diary. This method of recording data is extremely tedious and prone to errors and omissions. Even in the best-case scenario, when the historical records are complete, the insight that can be obtained is limited without reconfiguring and/or interpreting and/or curating (e.g., selecting relevant data for output to a user) the recorded data into a format that may assist with evaluating trends and supporting therapeutic modifications. As a result, most patients do not properly maintain their logbook or otherwise recorded data, which reduces the ability of the patient and the doctor to properly diagnose and manage the disease, which can ultimately result in poor adherence to therapy and poor glycemic control. Accordingly, a system is needed to automatically capture, store, transfer, curate and otherwise enable optimal assessment of the varied and voluminous data used to properly diagnose and treat diabetes.

As noted above, integrated diabetes management (IDM) systems and methods are described herein. As will be appreciated by one skilled in the art, there are numerous ways of carrying out the examples, improvements, and arrangements of the IDM systems (and methods) in accordance with embodiments of the present invention disclosed herein. Although reference will be made to the illustrative embodiments depicted in the drawings and the following descriptions, the embodiments disclosed herein are not meant to be exhaustive of the various alternative designs and embodiments that are encompassed by the disclosed invention, and those skilled in the art will readily appreciate that various modifications may be made, and various combinations can be made, without departing from the invention.

In addition, the IDM systems can be used to manage other types of diseases involving collection, analysis and dissemination of information to assist disease stakeholders (e.g., patients, care givers, health care providers, disease management companies, pharmacies, disease management-related product suppliers, insurers and other payers) in management of one or more diseases. Although described throughout this application with reference to the example of diabetes, this disclosure is not intended to be limited only thereto. For example, the system can be used (or modified for use) for integrated management of a wide number of other diseases or conditions.

Further, the IDM systems can be used by many types of people, including, but not limited to, diabetic patients, non-diabetic persons, caregivers, and healthcare professionals or healthcare entities such as disease management companies, pharmacies, disease management-related product suppliers, insurers and other payors. For ease of description, this disclosure describes the IDM system with reference to users. Reference to "users" is intended to encompass all types of users, without limit. Further, in some instances, this disclosure refers to patients or diabetic patients. This is done in the context of a non-limiting example, and is not intended to be limiting. Thus, reference to patients or diabetic patients is intended to refer to users of all types, without limit.

In addition, the IDM systems are understood to be useful to manage other types of diseases involving collection, analysis and dissemination of information to assist disease stakeholders (e.g., patients, care givers, health care providers, disease management companies, pharmacies, disease management-related product suppliers, insurers and other payers) in management of one or more diseases. Although described throughout this application as an integrated diabetes management system, this disclosure is not intended to be limited only thereto. For example, the system can be modified for use of integrated management of a wide number of other diseases or conditions. For ease of description, however, the system will be described with reference to diabetes as an illustrative example. Further, the IDM system can be used by many types of people, including, but not limited to, diabetic patients, non-diabetic persons, caregivers, and healthcare professionals or healthcare entities such as disease management companies, pharmacies, disease management-related product suppliers, insurers and other payors. For ease of description, this disclosure describes the IDM system with reference to users. Reference to "users" is intended to encompass all types of users, without limit. Further, in some instances, this disclosure refers to patients or diabetic patients. This is done in the context of a non-limiting example, and is not intended to be limiting. Thus, reference to patients or diabetic patients is intended to refer to users of all types, without limit.

As will become apparent from the following description, the IDM systems described herein allows users to access simple, quick, and readily available counseling information regarding a healthy diabetic lifestyle. The IDM systems can engage users in a manner that encourages them to maintain continuous (e.g., daily, weekly, or monthly) interaction with the IDM systems to gain knowledge about diabetes and encourage them to lead an increasingly healthy lifestyle. Diabetes patients who engage with an IDM system such as described herein will feel more in control of their diabetes management, which, in turn, will help them be in control leading to better patient outcomes. In some embodiments, the more a diabetic patient engages with the IDM system, the more satisfied they will feel with their life with diabetes (providing a desirable feeling of control). The IDM systems can use engagement, behavior design, and behavior change approaches to tailor the experience to each diabetic patient. The more a diabetic patient feels satisfied with his or her life with diabetes, the more his or her disease will be in control. The IDM system experiences can be designed to create more contextual, meaningful education that leads to more self-efficacy. The more the disease is in control, the better the clinical outcomes will be.

In an illustrative embodiment, the IDM systems include an interactive interface that is simple and engaging, and that provides a scalable means for users to seek information and support when needed so that they feel more in control of their condition. The interactive interface can be accessible over a network, such as the internet. A user may access the interactive interface via any internet enabled device, such as a smartphone, tablet, laptop, computer, or other type of device. In some embodiments, the interactive interface is accessible via an application installed on an internet-enabled device. In some embodiments, the interactive interface is available at a website. In some embodiments, the interactive interface is a chatbot (e.g., a computer program designed to simulate conversation with human users), although this disclosure is not intended to be limited to only this example. In some embodiments, the interactive interface interacts with users via prompts and selected responses. In some embodiments, the interactive interface responds to questions entered by the user. In some embodiments, inputs from the user to the interactive interface are spoken or typed. In some embodiments, responses from the interactive system to the user are audible or written. In some instances, the interactive interface may forward user questions to a real person, such as a healthcare professional, for response.

In an illustrative embodiment, one or more features of the IDM system are based on behavioral science techniques that are designed to modify patient behavior. For example, behavioral science teaches that diabetic patients (like all people) have a universal desire or need to feel good or feel better. Diabetes, however, violates this universal need because it makes diabetic patients feel bad or worse. In an illustrative embodiment, the IDM system counters this negative effect of diabetes by providing opportunities to satisfy one or more of the following additional diabetic desires: eating favorite foods, maintaining a healthy lifestyle, recovering from a relapse to unhealthy habits, receiving emotional rewards, having urgent questions answered, interacting with other people, and gaining insights and feeling smart, among others. By providing opportunities to satisfy one or more of these desires, the IDM system reinforces positive habits leading to behavioral change.

In an illustrative embodiment, the IDM system is beneficial for all types of diabetic patients, including those with type 1 diabetes, type 2 diabetes, or a pre-diabetic condition.

In an illustrative embodiment, the IDM system provides users with access to information regarding healthy substitutions for commonly favored foods that are unhealthy. In an illustrative embodiment, the IDM system provides access to frequent questions about diabetes. In an illustrative embodiment, the IDM system stores information regarding a user's interactions with the system and uses the stored information in future interactions to customize content for the user based on his or her preferences. In an illustrative embodiment, the IDM system stores information regarding a user's interactions with the system and follows up with the user after the interaction (e.g., hours, days, weeks after the interaction). For example, if the IDM system recommends a healthy substitution for an unhealthy food, the IDM system may follow up the next day to ask whether the user enjoyed the healthy substitution.

In one illustrative embodiment, the IDM system uses uploaded user health information to customize interactions with users. User health information can include data entered via the interactive interface, data uploaded from internet-enabled ("smart") devices (such as smart insulin pens or pumps, diabetes monitors, fitness trackers, diet trackers, etc.), and other types of information. The IDM system can analyze the uploaded health information to provide customize information for the user.

In the following description, specific details are given to provide a thorough understanding of the examples. However, it will be understood by one of ordinary skill in the art that the examples may be practiced without these specific details. For example, components/devices may be shown in block diagrams in order not to obscure the examples in unnecessary detail.

Certain examples are described as a process, depicted as a flowchart, a flow diagram, or a block diagram. Although a flowchart may describe the operations as a sequential process, many of the operations can be performed in parallel, or concurrently, and the process can be repeated. In addition, the order of the operations may be rearranged.

Example Devices that can Interface with the IDM Systems and Methods

FIG. 1 is a block diagram that illustrates an integrated diabetes management (IDM) system 100 according to one embodiment. Before considering the system 100, several additional devices that can communicate with the IDM system 100 over a network 5 will be described. In the illustrated embodiment of FIG. 1, these additional devices include an internet-enabled user device 10, a smart diabetes monitor 12, a smart insulin pen 14, a smart insulin pump 16, and a fitness tracker 18. These illustrated devices are provided by example only and other types of devices can also connect to the system 100 over the network 5. In some embodiments, one or more of these devices may be omitted and/or additional devices may be included.

The internet-enabled user device 10 can be any type of internet-enabled device without limit, including, a smartphone, tablet, laptop, computer, personal digital assistant (PDA), smartwatch, etc. In some instances, the internet-enabled user device 10 is a mobile device, such as any mobile device known in the art, including, but not limited to, a smartphone, a tablet computer, or any telecommunication device with computing ability, a mobile device connection module, and an adaptable user interface such as, but not limited to a touchscreen. A user typically possesses an internet-enabled user device 10, which can be used for various functions, such as sending and receiving phone calls, sending and receiving text messages, and/or browsing the internet.

The internet-enabled user device 10 can include a communication module that can be connected to the network 5, for example to communicate with the IDM system 100 and/or additional devices over the network 5. The communication module can be connected to the network 5 by wired or wireless communication, cellular communication, Bluetooth®, ZigBee®, LAN, WLAN, RF, IR, or any other communication method or system known in the art.

The internet-enabled user device 10 can include an input. The input can be a touchscreen, keypad, keyboard, mouse, microphone or any other type of input known in the art without limit. The input allows the user to enter information that can be transmitted to the IDM system 100 over the network 5. In some embodiments, the user uses the input to enter question or data for the IDM system 100. In some embodiments, the user uses the input to select from among options presented by the IDM system. The internet-enabled user device 10 can include a display. The display can include a screen and/or speaker. The display can display (e.g., visually or audibly) information received from the IDM system 100 to the user, such as answers to the user's questions and/or or prompts.

In an illustrative embodiment, the internet-enabled user device 10 communicates with the IDM system 100 over the network 5. This allows the user to interact with the IDM system 100 from any location that can access the network 5. Because many users commonly have an internet-enabled user device 10 that can access the internet over a cellular network with wide coverage, access to the IDM system 100 can be nearly constantly available to the user. This allows the user to interact with the IDM system 100 whenever desired. The availability of the IDM system 100 can increase its efficacy.

The smart diabetes monitor 12 can be any type of internet-enabled diabetes monitor without limit. The smart diabetes monitor 12 can be configured to measure a user's blood glucose level. There are typically two methods for measuring a user's blood glucose level. One method uses an electronic blood glucose meter. A sample of blood is obtained by piercing the skin of a user with a lancet. The sample of blood is then placed on a chemically-active test-strip, which interfaces with the blood glucose meter. Within several seconds of inserting the test-strip into the blood glucose meter, the blood glucose level of the user is read and shown on the digital display of the blood glucose meter.

The blood glucose meter method provides an accurate snapshot of a user's blood glucose level at a single moment in time. However, the blood glucose meter method does not indicate whether the user's glucose level is rising, falling, or steady. Additionally, the blood glucose meter method fails to capture a user's changing blood sugar levels after meals, between meals, and during the night.

An alternative improved method for measuring a user's blood glucose level in a continuous or real-time basis is to use a continuous glucose monitor (CGM) system. A CGM system generally includes a sensor, a transmitter, and a receiver (such as a handheld receiver). Some CGM systems use a glucose oxidase sensor. Some CGM devices use glucose binding protein (GBP) sensors. GBP CGM sensors may be preferred because they may be able to provide faster response times and better stability at lower cost than glucose oxidase based sensors. More information on glucose binding proteins and continuous glucose monitors can be found in U.S. Pat. Nos. 6,855,556, 7,496,392, 7,787,923, 7,792,561, 7,851,593, and 8,623,639, the entire contents of each of which are hereby incorporated by reference.

The smart diabetes monitor 12 can be either type of monitor described above or any other type of diabetes monitor. In an illustrative embodiment, the smart diabetes monitor 12 uploads information regarding a user's blood glucose level measurements to the IDM system 100. The measured blood glucose level and the time of measurement can be uploaded to the IDM system 100. In some embodiments, uploaded blood glucose level measurements are further associated with recently eaten foods and/or physical activity and this information can be uploaded to the IDM system 100 as well.

In some embodiments, a conventional (in other words, non-internet-enabled diabetes monitor) can be used. Measurements from the conventional diabetes monitor can be entered or otherwise obtained via the internet-enabled user device 10 and uploaded to the IDM system 100 over the network 5.

The smart insulin pen 14 can be any internet-enabled device for self-injection of insulin without limit. Insulin pens typically provide the ability for a user to set and inject a dose of insulin. Accordingly, a user can determine how much insulin they need and set the appropriate dose, then use the pen device to deliver that dose. In an illustrative embodiment, a smart insulin pen 14 transmits information regarding the timing and dose of an insulin injection to the IDM system 100 over the network 5. In some embodiments, information about uploaded insulin injections is further associated with recently eaten foods or physical activity and this information can be uploaded to the IDM system 100 as well.

In some embodiments, a conventional (in other words, non-internet-enabled) insulin pen can be used. Information about insulin injections from conventional insulin pens can be entered or otherwise obtained via the internet-enabled user device 10 and uploaded to the IDM system 100 over the network 5.

The smart insulin pump 16 can be any type of well-known internet-connected insulin pump. Some diabetic patients use insulin pumps to deliver a basal rate of insulin continuously. Insulin pumps may also provide bolus doses of insulin as needed. Insulin pumps may be considered an improvement over insulin pens because they deliver insulin continuously, rather than episodically. They can include a refillable or replaceable insulin reservoir. They can also avoid most of the needle sticks associated with insulin pens.

Patch pumps are insulin delivery devices that generally fall between insulin pens and sophisticated insulin pumps. Patch pumps may be disposable devices that stick to the patient's skin, and include an insulin reservoir, and a cannula insertion mechanism. Patch pumps may have, but do not require, electronics. They can include a reservoir of insulin containing a supply of insulin (e.g., a three-day supply) for delivery to the patient. Patch pumps may provide a basal rate of insulin, either electronically or mechanically metered, and may also optionally provide bolus doses. There are some patch pumps that deliver only bolus doses. Patch pumps are often disposable after their roughly three days of use, but some patch pumps may include both durable and disposable components.

The smart insulin pump 16 can be a traditional insulin pump, a patch pump, or any other type of insulin pump. The smart insulin pump 16 can upload information regarding the delivery of insulin to the patient to the IDM system 100 over the network 5. In some embodiments, the smart insulin pump 16 uploads information regarding the rate and quantity of insulin delivered by the pump.

In some embodiments, a conventional (in other words, non-internet-enabled) insulin pump can be used. Information about insulin delivery by the conventional insulin pump can be entered or otherwise obtained via the internet-enabled user device 10 and uploaded to the IDM system 100 over the network 5.

The fitness tracker 18 can be any device which measures (or otherwise obtains) health information (or other types of information) about the user. The fitness tracker 18 can be a device which measures patient vitals. In an illustrative embodiment, patient vital data includes, but is not limited to, heart rate, blood pressure, temperature, blood oxygen level, and/or blood glucose level. The patient vital data measurement values can be measured using sensors on the fitness tracker 18.

In an illustrative embodiment, the health information measured by the fitness tracker 18 can include caloric information (e.g., intake or expense of calories). The calorie intake information can be determined according to food items taken or about to be taken, selected from a list by the user. A calorie value list can be stored on the fitness tracker 18, the internet-enabled user device 10, on the IDM system 100, or on an additional device (e.g., a device accessible over the network 5).

In an illustrative embodiment, caloric expense information can be determined according to data from fitness tracker 18. The fitness tracker 18 can provide activity and/or caloric information about a user, including, but not limited to, physical movements, exercise, sleep pattern, and caloric consumption information, or any other patient data that may affect a caloric value about the patient.

The fitness tracker 18 can be a smart device. That is, the fitness tracker 18 can be network enabled. In some embodiments, the fitness tracker 18 connects to the network 5 directly. In some embodiments, the fitness tracker 18 connects to the network 5 via the internet-enabled user device 10. For example, the fitness tracker 18 can be communicatively coupled, locally or remotely, with the internet-enabled user device 10.

The health information measured by the fitness tracker 18 can be uploaded to the IDM system over the network 5.

As will be described below in greater detail, in an illustrative embodiment, the information uploaded to the IDM system 100 by the internet-enabled device 10, the smart diabetes monitor 12, the smart insulin pen 14, the smart insulin pump 16, and/or the fitness tracker 18 (or one or more additional devices) can be associated with a particular user. The information can be used to customize interaction between the user and the IDM system 100, for example, allowing the IDM system 100 to provide better answers or recommendations for the user. In some embodiments, the IDM system 100 analyzes the uploaded information to evaluate the health of the user. The IDM system 100 may provide alerts if uploaded information reveals a problem condition. The IDM system 100 may also provide recommendations for correcting the problem condition. The IDM system 100 may provide positive reinforcement or encouragement when to the user based on analysis of the uploaded information. For example, if analysis reveals that the user is doing well managing his or her diabetes, the IDM system 100 may encourage the user to continue beneficial behaviors. In some embodiments, the IDM system 100 communicates with the smart insulin pen 14 or smart insulin pump 16 to control the amount or timing of insulin delivered to the user by these devices.

Also shown in FIG. 1, is a web server 20. The web server may provide online content 22, which can be referred to, referenced by, or otherwise used by the IDM system 100. In an illustrative embodiment, the web server 20 provides a website accessible by users over the network 5. The website can include online content 22 related to diabetes, food choices, exercise, or other topics. As will be described below, the IDM system 100 can link users to the web server 20 to access the online content 22 in response to user questions.

The network 5 can include any type of communication network without limit, including the internet and/or one or more private networks, as well as wired and/or wireless networks.

Example IDM Systems and Methods

The IDM system 100 will now be described with reference to the embodiment illustrated in FIG. 1. The IDM system 100 may be embodied in a single device (e.g., a single computer or server) or distributed across a plurality of devices (e.g., a plurality of computers or servers). The modules or elements of the IDM system 100 can be embodied in hardware, software, or a combination thereof. The modules or elements may comprise instructions stored in one or more memories and executed by one or more processors.

Each memory can be a RAM memory, a flash memory, a ROM memory, an EPROM memory, an EEPROM memory, a register, a hard disk, a removable disk, a CD-ROM, or any other form of storage medium known in the art. Each of the processors may be a central processing unit (CPU) or other type of hardware processor, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or in the alternative, the processor may be any conventional processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration. Exemplary memories are coupled to the processors such that the processors can read information from and write information to the memories. In some embodiments, the memories may be integral to the processors. The memories can store an operating system that provides computer program instructions for use by the processors or other elements included in the system in the general administration and operation of the IDM system 100.

In the illustrative embodiment shown in FIG. 1, the IDM system 100 includes a user interface 120, an interactive engine 130, a user database 140, and a content database 150. In some embodiments, one or more of these elements can be omitted. In some embodiments, the IDM system 100 contains additional elements.

The user database 140 can comprise a single database or a plurality of databases. In an exemplary embodiment, users of the IDM system 100 each have an account with the IDM system 100. Information regarding user accounts can be stored in the user database 140. The user database 140 can also store additional information associated with the user account. For example, the user database 140 can store IDM history data 142 and uploaded health data 144.

In an illustrative embodiment, IDM history data 142 is data generated and stored during a user's previous interactions with the IDM system 100. This can include previous inquiries submitted by the user; previous responses provided by the user; user-entered preferences; and/or a log indicating the timing of the user's interactions with the IDM system 100, among other things. The IDM system 100 can automatically add IDM history data 142 as the user continues to use and/or interact with the IDM system 100. The IDM history data 142 can be used by a predictive analytics module 136 and a machine learning module 138 of the interactive engine 130 (or other modules of the IDM system 100) to customize future interactions between the IDM system 100 and the user. As a user uses the IDM system 100, the IDM history data 142 associated with the user's account in the user database 140 grows, allowing the IDM system 100 to know the user better, provide better content, and create a more engaging experience. In some embodiments, this increases the efficacy of the IDM system 100.

The user database 140 also stores uploaded health data 144 associated with a user's account. The uploaded health data 144 can include the information entered by a user on the internet-enabled user device 10 or uploaded by the smart diabetes monitor 12, smart insulin pen 14, smart insulin pump 16, and/or fitness tracker 18 (described above). The uploaded health data 144 can also include additional information produced by the IDM system 100 upon analysis of the user's uploaded data. For example, upon analysis of the user's uploaded data, the IDM system may generate health trend information, which can also be stored among the uploaded health data 144 associated with the user's account in the user database 140. In some embodiments, uploaded health data 144 can include information uploaded or entered by a healthcare provider (such as a doctor).

In the illustrative embodiment, the IDM system 100 also includes a content database 150. The content database 150 can be a single database or a plurality of databases. The content database 150 includes content that is delivered to users during user interaction with the IDM system 100. The content can include diabetes education information. In some instances, the content is developed, selected, and/or curated by healthcare professionals, such as doctors or CDEs. The content can be similar to that which is provided by healthcare professionals during in-person counseling sessions. However, content on the IDM system 100 is available to the user at any time and accessible, for example, on the internet-enabled device 10.

In the illustrated embodiment, the content database 150 includes food content 152, diabetes information content 154, and activity content 156. In an illustrative embodiment, food content 152 can be developed and curated to encourage users to eat healthy, while still allowing them to eat foods that they enjoy. Food content 152 can include a database of unhealthy, common favorite foods as well as diabetic-friendly and healthy alternatives and recipes. For example, food content 152 can identify pizza as a commonly favored, unhealthy food choice and provide information regarding several healthy pizza alternatives (see, for example, FIGS. 4A-4F described below). The food content 152 can be developed to allow users to continue to eat foods they enjoy, while also improving their diet. Food content 152 can also include answers to common questions diabetic patients ask about food. Other types of food content 152 are possible. In some embodiments, the food content 152 is locally stored on the content database 150. In some embodiments, the food content 152 includes links to externally available information, for example, online content 22 on the web server 20. In some embodiments, the food content 22 includes a database of caloric information for certain foods.

Diabetes information content 154 can be developed and curated to provide answers to common questions asked by diabetic patients. For example, one of more healthcare professionals can develop a list of questions commonly asked by diabetic patients. The healthcare professionals can develop content for responding these questions. This diabetes information content 154 is stored in the content database 150. In some embodiments, diabetes information content 154 is generated in response to user interactions with the IDM system 100. For example, a user may enter a diabetes related question. If the IDM system 100 does not include diabetes information content 154 addressing the question, the IDM system 100 can forward the question to a healthcare professional. The healthcare professional can provide responsive content which can be provided to the user and stored in the content database 150 for use in future interactions. Other types of diabetes information content 154 can also be included. In some embodiments, the diabetes information content 154 is locally stored on the content database 150. In some embodiments, the diabetes information content 154 includes links to publicly available information, for example, online content 22 on the web server 20.

Activity content 156 can be developed and curated to provide information about healthy lifestyle choices and physical activities for diabetics. The activity content 156 can be developed by healthcare professionals. In some embodiments, the activity content 156 is locally stored on the content database 150. In some embodiments, the activity content 156 includes links to publicly available information, for example, online content 22 on the web server 20.

Food content 152, diabetes information content 154, and activity content 156 are shown by way of example of certain types of content only, and other types of content can be included in addition to or in place of one or more of the illustrated types of content.

In an illustrative embodiment, content in the content database 150 can be stylized in the "personality" of the integrated diabetes management system 100. That is, content can be authored or written in a manner that provides engaging interactions having a similar look and feel over time.

The IDM system 100 can include a user interface 120 and an interactive engine 130. The user interface 120 can provide an interface by which the IDM system 100 interacts with or displays information to users. The user interface 120 can be accessible to the user over the network 5. For example, a user can access the user interface 120 on the internet-enabled user device 10. The user interface 120 can include an interactive interface 122 and a user data viewer 124. In some embodiments, the interactive interface 122 is an interactive application, such as a smartphone, tablet, or computer application. In some embodiments, the interactive interface 122 is an interactive website. In a non-limiting example, the interactive interface 122 is a chatbot.

The interactive interface 122 relays inputs and outputs between a user and the interactive engine 130. The interactive engine 130 processes inputs and outputs to provide an interactive experience for the user. The interactive engine 130 also retrieves information from the user database 140 and the content database 150. For example, in interacting with a user, the interactive engine 130 may access the user database 140 to obtain the user's IDM history data 142 and uploaded health data 144. In an illustrative embodiment, the interaction with the user is customized based on the user's IDM history data 142 and uploaded health data 144. Similarly, the interactive engine 130 can retrieve content from the content database 150. The interactive engine 130 can retrieve content from the content database 150 based on user inputs (e.g., questions, responses, and selections), as well as user information stored in the user database 140. Through the interactive interface 122, the interactive engine 130 provides engaging and informative interactions with the user that allows the user to feel in control of his or her diabetes management and gain diabetes education.

The interactive engine 130 can include a natural language processor 132, a response generator 134, a predictive analytics module 136, and a machine learning module 138. In some embodiments, one or more of these elements can be omitted or combined with another element. In some embodiments, the interactive engine 130 contains additional elements.

The natural language processor 132 and the response generator 134 can allow the interactive interface 130 to provide a simple interaction experience via the interactive interface 122. For example, in an illustrative embodiment, the natural language processor 132 and the response generator 134 allow a user to have an interactive chat (written or spoken) with the IDM system 100.

The natural language processor 132 can parse user inputs into a machine-understandable format. For example, in an illustrative embodiment, the interactive interface 122 allows a user to enter a natural language question. The natural language processor 132 can parse the question such that it can be understood by the interactive engine 130. As another embodiment, the interactive interface 122 can allow the user to speak a question. The natural language processor 132 can include a voice recognition module that can recognize the spoken question and parse the question such that it can be understood by the interactive engine 130.

The response generator 134 formulates responses to user inputs. The response generator 134 can receive information from the natural language processor 132. In an illustrative embodiment, responses generated by the response generator 134 include an answer to the user's question. Alternatively, the responses can include requests for additional information from the user. The request for additional information can be provided as a question prompt or one or more options from which the user can select. The response generated by the response generator 140 can be stylized in the "personality" of the integrated diabetes management system 100 as mentioned above.

The interactive engine 130 can also include a predictive analytics module 136 and a machine learning module 138. In an illustrative embodiment, the predictive analytics module 136 uses information in the user database 140 (such as IDM history data 142 and uploaded health data 144) to predict content that a user will enjoy or that will be beneficial to the user. For example, based on uploaded health data 144, the predictive analytics module 136 can select content to present to the user designed to help the user manage his or her blood sugar. As another example, based on IDM history data 142 that indicates that a user frequently asks about pizza, the predictive analytics module 142 can select new pizza related content to display the user. In some instances, the response generator 134 accesses the predictive analytics modules 136 in generating responses to be provided to the user.

In an illustrative embodiment, the machine learning module 138 analyzes information in the user database 140 (such as IDM history data 142 and uploaded health data 144) to provide inputs which can be communicated to the predictive analytics module 126. For example, the machine learning module 138 can learn about a user based on past interactions with the IDM and generate data which is used by the predictive analytics module 136 to customize content for future interactions. Thus, the more a user interacts with the IDM system 100, the more personalized interaction with the system will become. In some instances, personalized interaction increases the efficacy of the IDM system 100.

The user interface 120 can also include a user data viewer 124. The user data viewer 124 can be a portal which allows a user to access information related to their account. For example, a user can log into the user data viewer to view uploaded health data 144. In some embodiments, the user data viewer 124 can provide a gateway for connecting patients and healthcare professionals. In some embodiments, healthcare professionals can access the user data viewer 124 to view information about the user.

Figure 2:
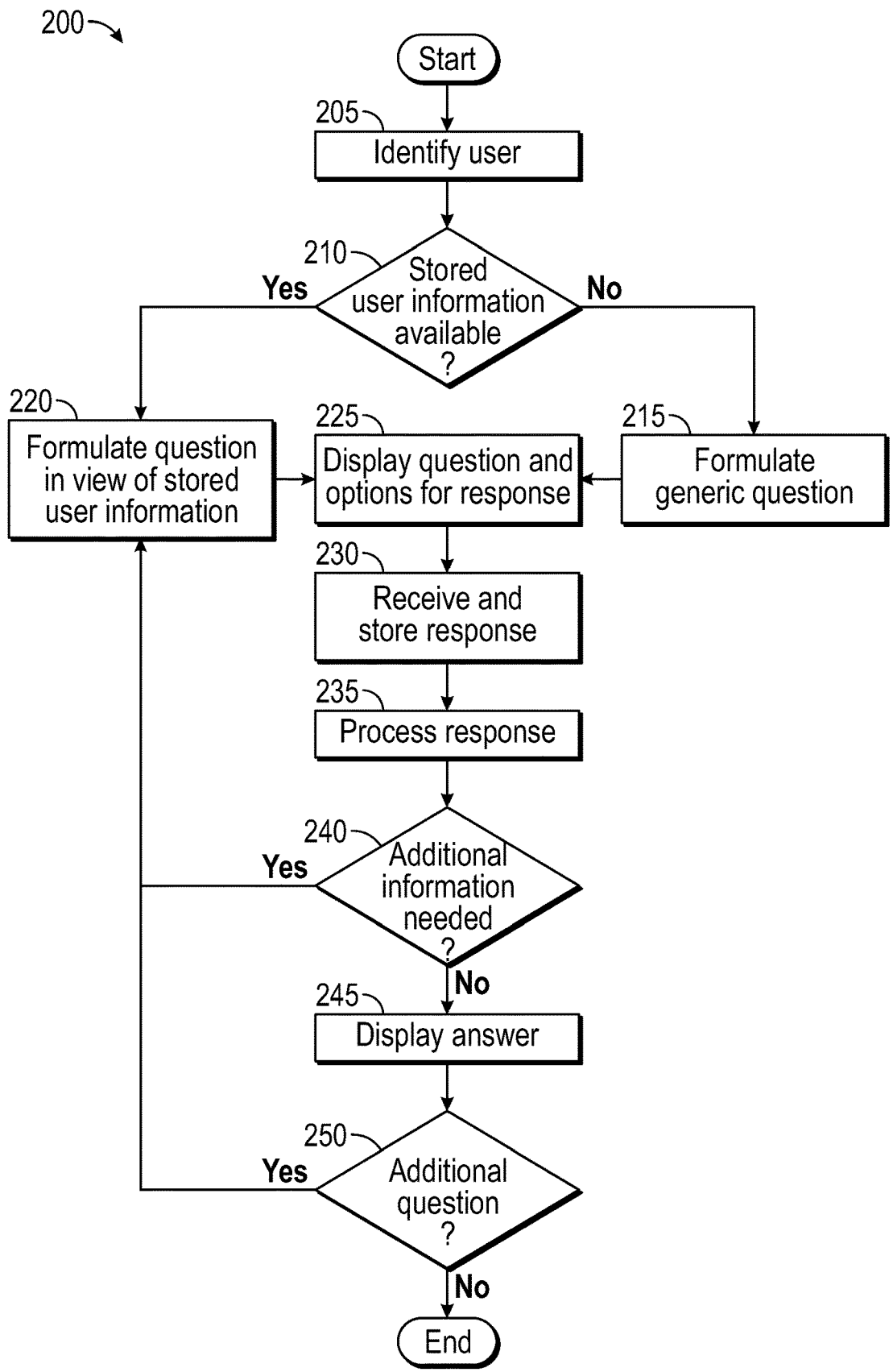
FIG. 2 is a flowchart illustrating an example process for the IDM system of FIG. 1.

FIG. 2 is a flowchart illustrating an example process 200 used by the interactive module 130 of the IDM system 100 to interact with a user via the interactive interface 122. The process 200 begins at a start step, and then moves to a step 205, wherein the IDM system 100 identifies a user. This can occur when a user logs into the IDM system 100 or opens an IDM system application. The user can access the interactive interface 122 over the network 5 on an internet-enabled user device 10. Identification of a user can include looking up the user in the user database 140. After identification of the user, the process moves to decision step 210, wherein the IDM system 100 determines whether stored user information is available for the authenticated user. The stored user information can be associated with the user's account. The stored user information can include information stored in the user database 140, such as IDM history data and/or uploaded health data 144.

If stored user information is not available, possibly because the user has not previously interacted with the IDM system 100, the IDM system may move to a step 215 to formulate a generic question. For example, the generic question can ask the user what he or she wants to talk about or prompt the user to enter a question, among other things. The process then moves to step 225, where the question is displayed to the user as well as a list of options for response, from which the user can make a selection.

Returning to the decision step 210, if a decision was made that the stored user information is available (for example, IDM history data 142 stored during previous interactions with the IDM system 100 or uploaded health data 144), the IDM system 100 moves to step 220, wherein the IDM system 100 formulates a question for the user in view of the stored information. For example, the machine learning module 138 can analyze the stored information and the predictive analytics module 136 can make determinations about the question that is formulated. For example, the question can be formulated in an area in which the IDM system 100 understands that the user likes to discuss, or in an area that the IDM system 100 understands that the user needs to improve, among others. The process 200 then moves to the step 225, wherein the question is displayed along with several options for response.

From step 225, the process 200 moves to a step 230, at which a response is received from the user. The response can include a selection from among the displayed options. The selection can be made via an input on the internet-enabled user device 10. Further, at step 230, the response is stored, for example, written to the IDM history data 142 associated with the user's account in the user database 140. This allows the response to be used in future interaction between the user and the IDM system 100.

The process 200 then moves to step 235, where the user's response is processed. Processing of the response can be performed by the response generator 134. The process 200 then moves to a decision step 240, at which the response generator 134 (or another module of the IDM system 100) determines whether additional information is needed from the user in order to select content to display. If additional information is needed, the process moves back to step 220. If no additional information is needed, the process moves to step 245, wherein content is displayed to the user. The content can be selected by the response generator 134 from among the content stored in the content database 150. The content can be displayed via the interactive interface on a display the internet-enabled user device 10.

The process 200 then moves to a decision step 250, at which the IDM system 100 asks whether the user has additional questions. If the user selects "yes," the process returns to step 220. If the user selects "no," the process 200 ends.

As described, the process 200 allows the IDM system 100 to customize interactions with a user based on previously stored user information, by, for example, formulating specific questions for the user and/or selecting content to display to the user based on the previously stored information. Further, the process 200 may store responses received from the user, making additional information available to customize future interactions with the user.

Although illustrated as a prompt-based process which provides the user with options for response, the process 200 can be modified to allow a user to enter natural language questions and or responses. The natural language questions and response can be processed by the natural language processor 132.

Figure 3:
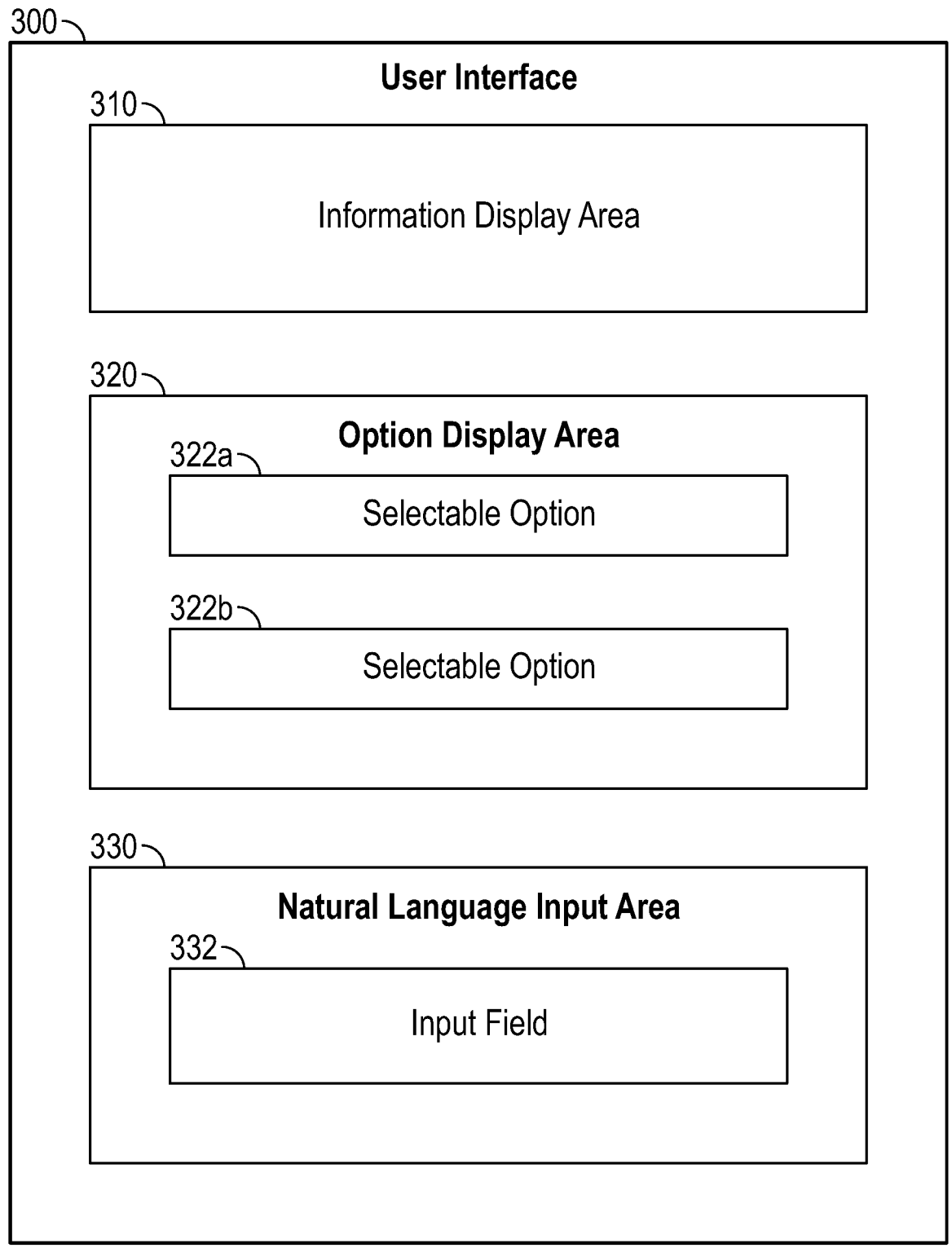
FIG. 3 illustrates an example user interface on a display of an internet-enabled user device accessing an interactive interface of the IDM of FIG. 1.

FIG. 3 illustrates an example user interface (or GUI) 300 on a display of an internet-enabled user device 10 accessing the interactive interface 122 of the IDM 100. The interface can be customized to suit the type of internet-enabled user device 10. For example, a more compact user interface can be used on smaller devices with smaller displays, such as smart phones.

In the illustrative embodiment of FIG. 3, the user interface 300 includes an information display area 310. The information display area 310 can present questions or other information from the IDM system 100. The user interface 300 also includes an option display area 320. The option display area 320 can display options from which a user can select a response. In the illustrated embodiment, two selectable options 322a, 322b are illustrated, although other numbers of options can be used in other embodiments. The user interface 300 also includes a natural language input area 330, which includes an input field 332. The natural language input area 330 allows the user to type (or otherwise enter) any question desired.

Figure 4B:
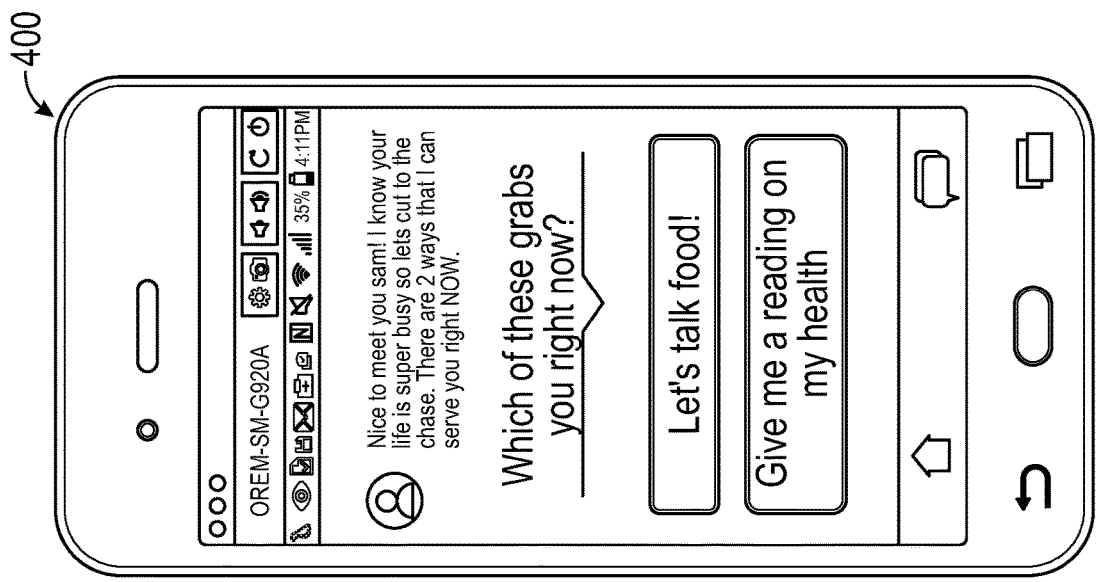
FIGS. 4A, 4B, 4C, 4D, 4E, and 4F illustrate example screens of the display of an internet-enabled user device accessing the IDM system of FIG. 1.
Figure 4A:
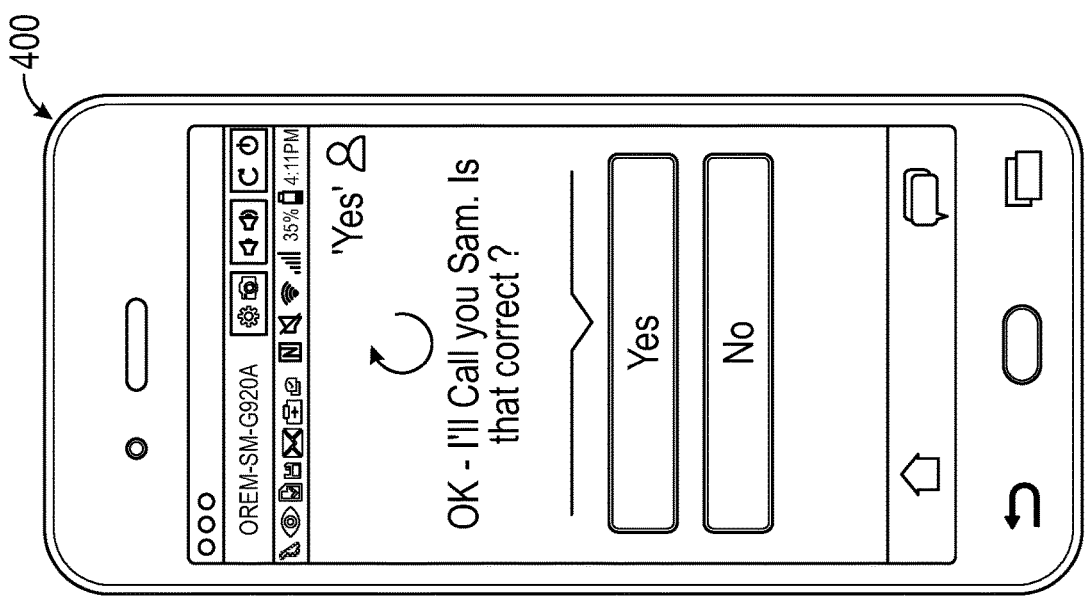

FIGS. 4A-4F illustrate examples screens that are presented to a user via a display 400 of an internet-enabled user device accessing the IDM system 100, according to one embodiment. These screens present select instances in an interaction between a user and the IDM system 100, and are not illustrative of every step or type of interaction. As illustrated in FIG. 4A, the display 400 offers "Yes" and "No" options for confirming the name by which the IDM system 100 will address the user. In an illustrative embodiment, the IDM system 100 asks the user his or her name and uses the user's name in future interactions to personalize the IDM system 100 for the user. The user's name can be stored in the user database 140.

In FIG. 4B, the display 400 poses a question ("Which of these grabs you right now?") to the user and offers options for response ("Let's talk food!" and "Give me a reading on my health"). As discussed above, the question and options presented can be customized based on previous user interactions with the IDM system 100. For example, the IDM system 100 may understand that this particular user frequently want to talk about food and discuss his or her health readings.

Figure 4D:
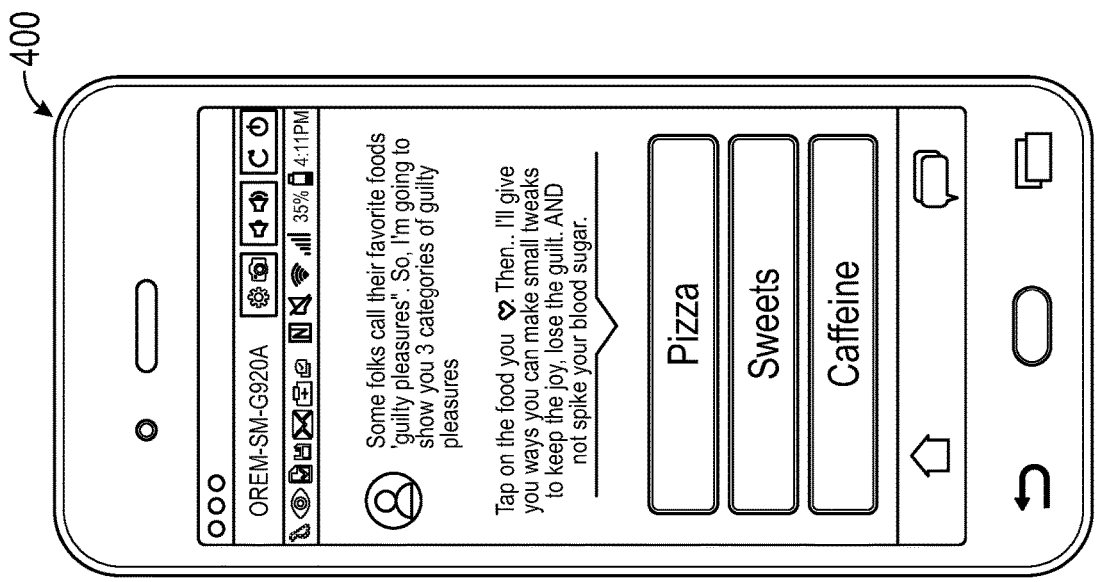
Figure 4C:
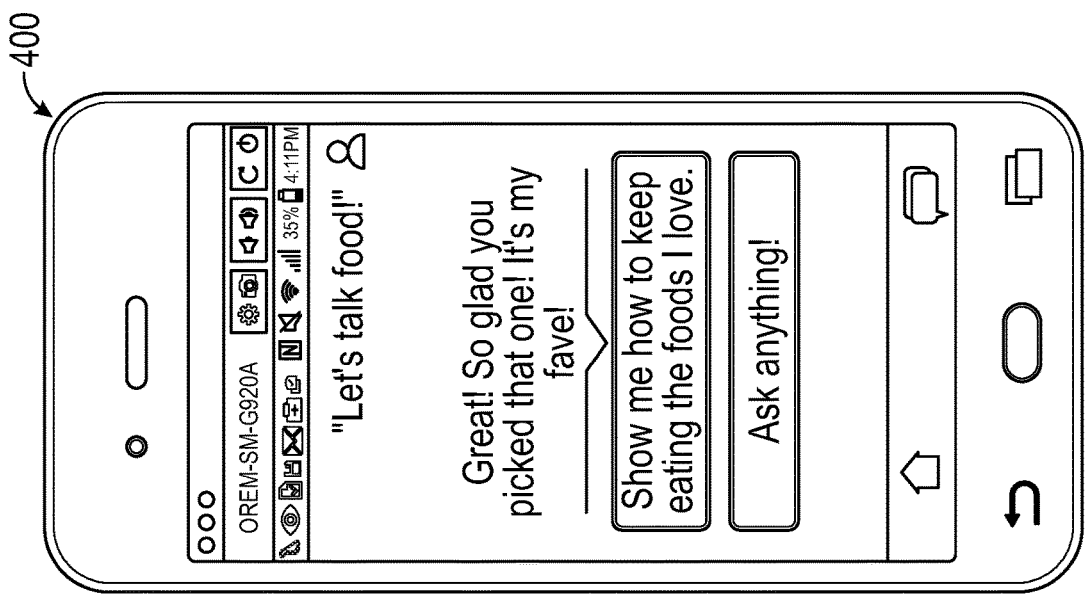

In FIG. 4C, the display 400 presents a response based on the user's selection. In the illustrated embodiment, the user selected "Let's talk food!" from among the options displayed in FIG. 4B. The IDM system 100 now presents additional options ("show me how to keep eating the foods I love" and "Ask me anything!) to acquire additional information that is needed to select content to display to the user. In the illustrated example, the option "Ask me anything!" allows a user to enter any natural language question.

In FIG. 4D, the display 400 presents a list of commonly favored unhealthy foods for which the IDM system 100 can provide diabetes related counseling (for example, healthy substitution options). In this illustrated embodiment, the user selected "Show me how to keep eating the foods I love" from among the options presented in FIG. 4C. In FIG. 4D, the display 400 now lists options for "Pizza," "Sweets," and "Caffeine." The displayed options can be based on previously stored user data and/or available content. In the illustrated example, the user selects "Pizza."

Figure 4F:
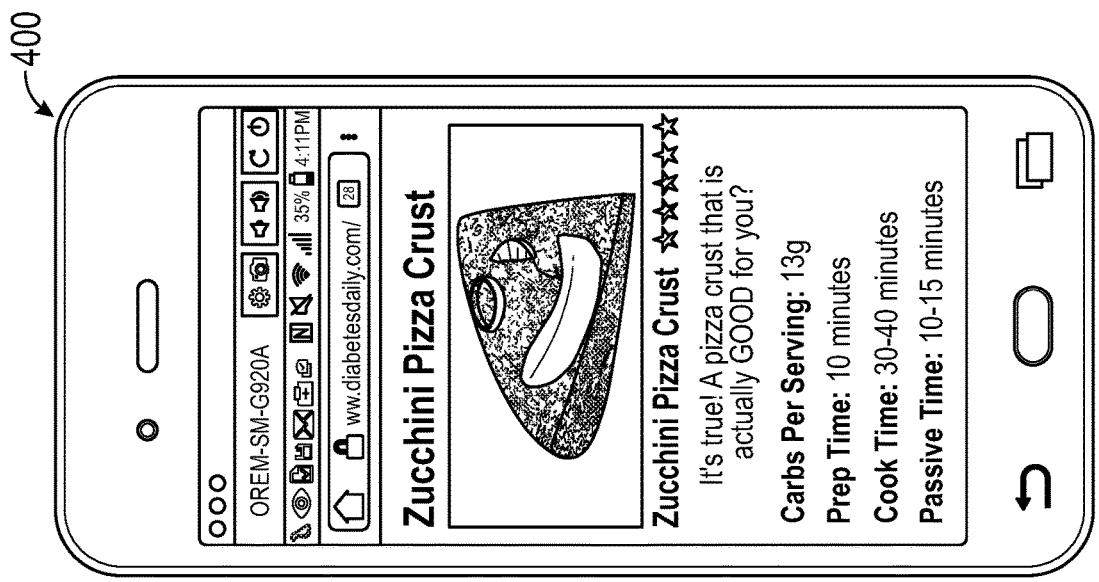
Figure 4E:
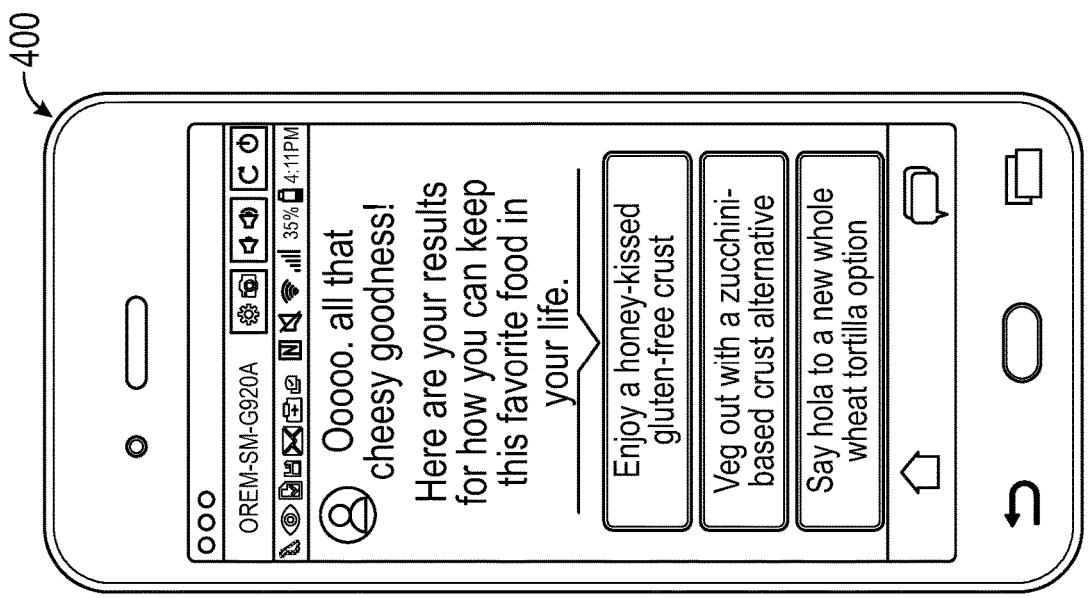

FIG. 4E illustrates the display 400 after the user selects "Pizza." The display 400 now shows results for how the user can keep this favorite food (pizza) in his or her life while still effectively managing his or her diabetes. The display presents options based on previously stored user data and/or available content. In the illustrated embodiment, the display 400 shows options for "Enjoy a honey-kissed gluten-free crust," "Veg out with a zucchini-based crust alternative," and "Say hola to a new whole wheat tortilla option." Each of these options will allow a user to access content that will still allow the user to eat pizza, while also managing diabetes in an effective way.

FIG. 4F illustrates the display 400 showing content after the user selects "Veg out with a zucchini-based crust alternative" from among the options in FIG. 4E. The illustrated content is an online recipe for a zucchini pizza crust. For example, the recipe can be online content 22 publicly available on web server 20.

The screens of the display 400 shown in FIGS. 4A-4F are provided by way of example only and are not intended to be limiting.

Figure 5:
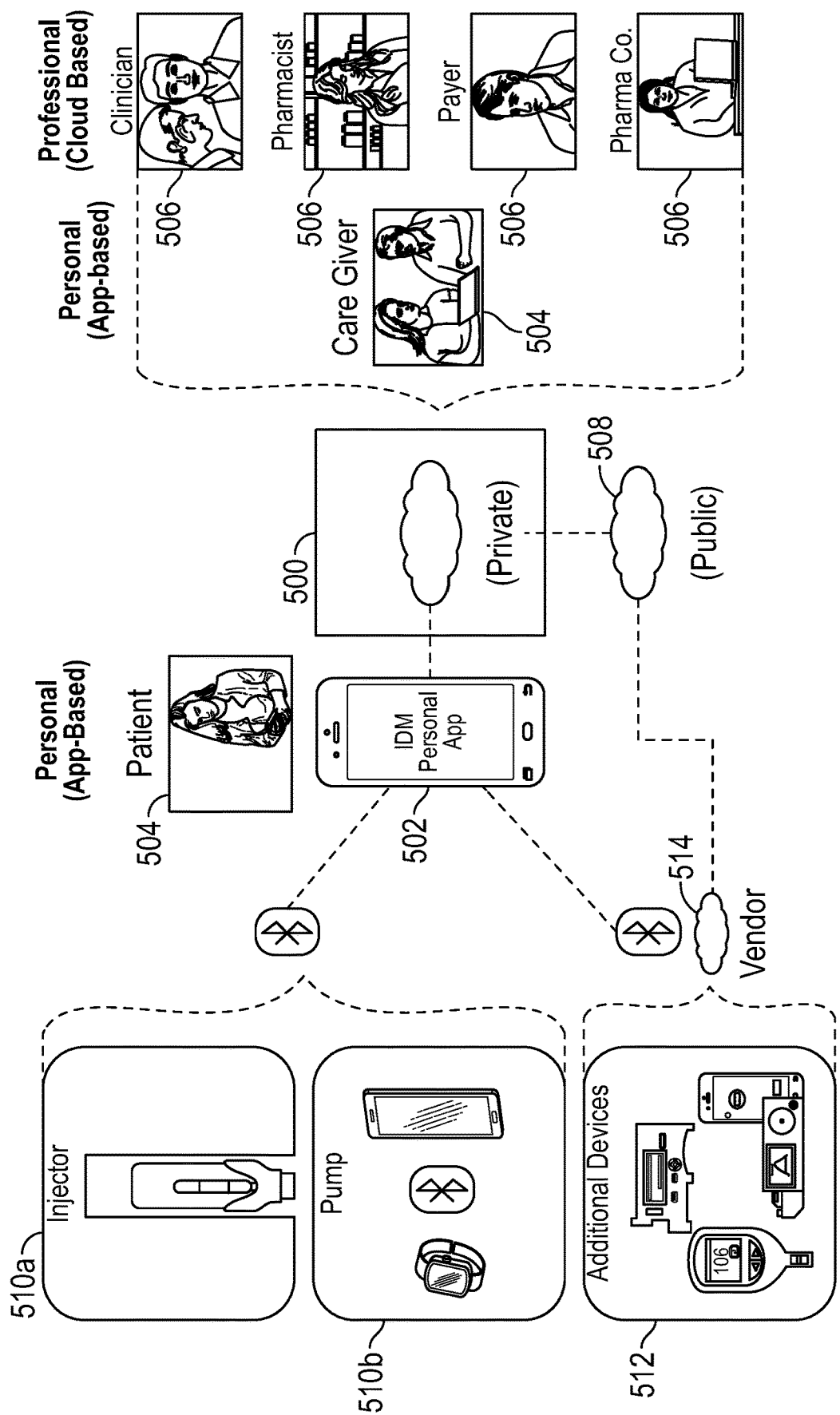
FIG. 5 is a block diagram illustrating an integrated diabetes management (IDM) system according to another embodiment.

FIG. 5 illustrates an IDM system 500 according to another embodiment. The IDM system 500 can be similar to the IDM system 100 in terms of hardware (not illustrated in FIG. 5) for performing analysis and employing artificial intelligence and machine learning to provide a customized experience for a user of the IDM system 500 such as an interactive engine 130 having a predictive analytics module 136 and machine learning module 138. The IDM system 500 can also include or have access to a user database 140 and a content database 150. For example, healthcare professionals or related organization(s) can develop recommended disease management protocols and recommended lifestyle choices for optimized patient outcomes and store this diabetes information content 154 in the content database 150. The IDM system 500 cam be configured to transmit data securely (e.g., encrypted) to a remote server such as a cloud storage server, to perform analysis of received data (e.g., disease management data), to provide feedback to the user (e.g., customized feedback with curated content based on a user's data and interface interactions), and send all or a portion of the data and/or curated content to another user device or remote health management access point (e.g., as cloud storage) where the information can be accessed by healthcare stakeholders, such as the patient's physician or other healthcare provider (HCP), family member or other caregiver, pharmacist, disease management company, medical supplier or payor. Conversely, alerts, reminders, and interventions can be provided to the user by the user's network, e.g. an HCP, securely through the IDM system 500.

User access to the IDM system 500 can be accomplished with user device 502 with an interactive interface that can be accessible via a web browser or an application (such as a phone application (app) for a smartphone or a computer application, for example). The user device 502 can be, but is not limited to, a smartphone, smart watch, tablet, laptop, computer, personal digital assistant ("PDA"), and the like. In some instances, the user device 502 is a mobile device, such as any mobile device known in the art, including, but not limited to, a smartphone, a tablet computer, or any telecommunication device with computing ability, a mobile device connection module, and an adaptable user interface such as, but not limited to a touchscreen. A user typically uses such a mobile device for various functions such as sending and receiving phone calls, sending and receiving text messages, and/or browsing the internet. The user device 502 communicates with the IDM system 500 via a wireless network and/or a wired network.

In accordance with an aspect of the illustrated embodiment in FIG. 5, the IDM system 500 operates in conjunction with an IDM personal application 504 and an IDM professional application 506 downloaded or otherwise installed on a user device 502. The IDM applications (e.g., the IDM personal application 504) can be operated in a cloud-dependent configuration whereby the mobile device with application transfers data to and receives data from a cloud (e.g., the IDM system 500) during an application session, for example, or periodically or continuously in the background, or can be operated in a distributed configuration whereby the application functions in a standalone mode and then connects as needed to selectively to the cloud (e.g., the IDM system 500).

For example, the IDM personal application can show as a single icon on a patient's device(s) 502. The IDM personal application 504 provides an interface to the IDM system 500 for a patient or a patient's caregiver for such functions and experiences as viewing dose data, texting with a clinician, adding meal data to the patient's stored data, importing blood glucose data, and so on. The IDM professional application 506 provides an interface to the IDM system 500 for other users such as a clinician, pharmacist, payer, pharmaceutical company or other medical company, among others, for such functions as viewing a patient's data or a patient population's data, texting a patient and performing dose titration, among other functions. The IDM personal (patient, caregiver) software 504 can comprise one or more applications, for example. The IDM professional (clinicians, pharmacists, etc.) software 506 can be web-based for different user types and provides a separate experience for the patient's care team providers, payers and pharmacists). For example, the IDM professional application 506 can be programmed to bring in data from patients' IDM personal apps 504.

With continued reference to FIG. 5, the user device 502 can be connected to other devices (e.g., via Bluetooth) such as one or more medication delivery devices (MDDs) 510 (e.g., an insulin injector 510*a* and/or or a pump indicated at 510*b*), and other devices such as glucose or lifestyle monitoring devices indicated generally at 512, which can be smart devices such as those indicated at 12, 14 and 16 in FIG. 1. For example, the other devices can include, but are not limited to, one or more of a carbohydrate input device or application running on a user's cellphone that allows the patient to input food and drink consumed, a device or related application having an oral medication input element that permits a user to track oral medications ingested, a BGM and/or CGM, and a device or application for inputting wellness data such as user activity level. The IDM personal application 504, once downloaded, allows the user to selectively activate additional functionality such as that associated with respective smart devices such as MDD(s) (e.g., an injection pen 14 app, pump 16 application or other dose capture app). An MDD application can provide device connectivity and data offload functions, and dose data storage and access functions, dose data to cloud transfer functionality, user profile creation and authentication functionality, connected third party experiences (e.g., interaction between the user and a third party such as a vendor for BG data tracking), and output and analysis of dose data and BGM data. With reference to FIG. 5, some device data can be sent to the user device 502 with IDM personal application 504 for storage on private cloud, whereas other data (e.g., non-proprietary or unregulated medical device data from devices) can be transmitted to a public cloud 508 by the devices or their vendor 514 for access by the user devices 502.

Similarly, the IDM professional application 506 can be selectively configured with different functionality by different stakeholders to include, for example, a patient population management sub-application, and a patient outcomes sub-app, and a data and communication protocols application programming interface (API) to enable transmission of data between users and systems. Some examples are a proprietary cloud or "closed API" that allows users to create accounts and gain direct access to data and functionality through application 506 views, a commercial cloud or "open API" wherein data is passed to another entity (e.g. Glooko) to facilitate use by the end-user (e.g., via an open API), or a hybrid model that simultaneously offers both of the above open and closed API options to utilize proprietary data generated from devices with closed APIs as well as data from devices with open APIs.

In accordance with an aspect of the embodiment illustrated in FIG. 5, one or more of the devices 510 and 512 are connected devices that can communicate data (e.g., delivered amounts of medication and blood glucose readings) directly to the IDM system 500. An example of a connected medication delivery device (MDD) is described in commonly owned U.S. application Ser. No. 14/485,749, filed Sep. 9, 2014, and incorporated by reference herein. A platform for connected device communication with the IDM system 500 is described below. The IDM system 500 and connected devices (e.g., MDDs 510 and other devices 512) advantageously provide an end-to-end IDM solution for people with diabetes and their care network (e.g., health care provider(s), caregiver(s), pharmacist and insurance company) to ease the burden of managing diabetes on the PATIENT as well as on other disease management stakeholders. This IDM solution transforms data to bring enhanced end user experiences for improved outcomes. This IDM solution can be implemented as a collection of products that broadly address needs associated with a specific medical condition such as diabetes, although the IDM solution can be configured to manage different medical conditions. The products can be hardware and/or software that deliver value to a defined group of people such as patients or caregivers, or professional disease management personnel such as health care provider, pharmacist and insurance company. The software products described herein (e.g., phone apps or computer applications) can comprise one or more modules, a module being understood to be collection of functionality that delivers a set of experiences such as discreet events, tasks, and actions, for example.

Figure 6:
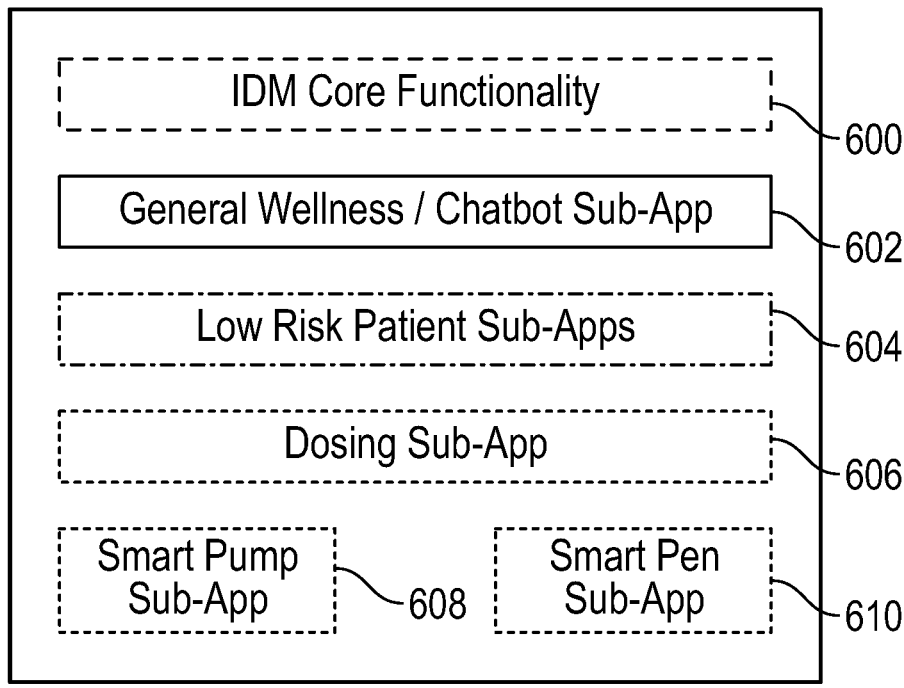
FIG. 6 depicts a platform for an IDM personal application portion of an IDM solution according to an illustrative embodiment.
Figure 6:
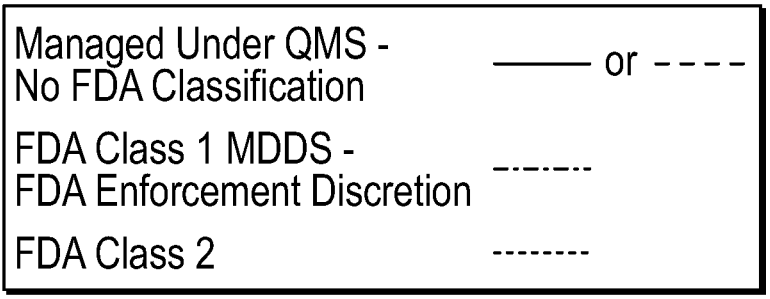

An example of a platform for an illustrative IDM personal application portion 504 of the IDM solution is depicted in FIG. 6. The medication delivery and monitoring devices 510 and 512 in FIG. 5 interact with the patient through the same IDM phone application 504 for ease of use. The IDM personal phone application 504 for the user device 502 can be programmed to comprise different components having varying degrees of regulatory compliance requirements in accordance with an illustrative embodiment. For example, the IDM personal phone application 504 can comprise a "wrapper" application that is a more loosely regulated than other components such as sub-apps that are more tightly regulated. For example, the wrapper application can be a Class 1 MDDS application (i.e., a quality system is required, but no regulatory filing is needed), whereas the sub-apps for medical device interactions or medical algorithms such as for an automated dose capture device require undergoing a regulatory approval process. The device sub apps can be purposefully kept minimal in function to reduce regulatory overhead.

With continued reference to the example IDM personal application 504 depicted in FIG. 6, the application 504 can have an IDM core functionality 600 that provides patient enrollment and security functions, that can selectively turn on/off additional modules, and that performs data sharing with the user's physician, external systems, and EMRs. A General Wellness/Chatbot sub-application 602 is provided for interactions with patients to encourage healthy self-care behaviors with respect to AADE7 Self-Care Behaviors™ such as eating, exercise, medications, and the like, and to provide curated educational and patient support content. Low Risk Patient sub-apps 604 can be provided that may need FDA Class 1 MDDS approval, that is, FDA enforcement discretion, since they control import of data from devices such as a BGM, insulin pumps, CGM, Fitbit (or other fitness trackers) and so on, export data to external systems such as Glooko, Healthkit, and so on, and can provide medication or other healthcare reminders. Higher controlled sub-applications 606 that require a FDA Class 2 classification can include, for example, an off-the shelf module to make recommendations for insulin dose based on patient's current and prior blood glucose trend and activity levels, and set upper and lower thresholds of amount of the dose.

The applications can be tiered according to regulatory requirements within the IDM system 500 platform which is advantageous because it allows for programmed regulated experiences to be kept as lean as possible to reduce ongoing maintenance. In addition, as many experiences as possible are programmed to occur in the IDM areas requiring minimal regulatory compliance to increase flexibility and speed of update process.

As described above, the user device 502 can include a display on which to generate screens by the IDM personal application 504 or IDM professional application 506, depending on the user. A number of example screens will now be described to illustrate some of the functions of the IDM personal application 504 and advantages of its operations with the IDM system 500 and connected devices 510 and 512 to create the end-to-end IDM solution such as data-driven insights, digital behavior follow-ups, profile-specific tips for disease management, advanced onboarding and progressive profiling. Such functionalities as personal guidance, a predictive chatbot and user profiling (e.g., based on inputted data and interactive information) and is of value to give the user curated content that is the right information at the right time for that user.

Figure 7:
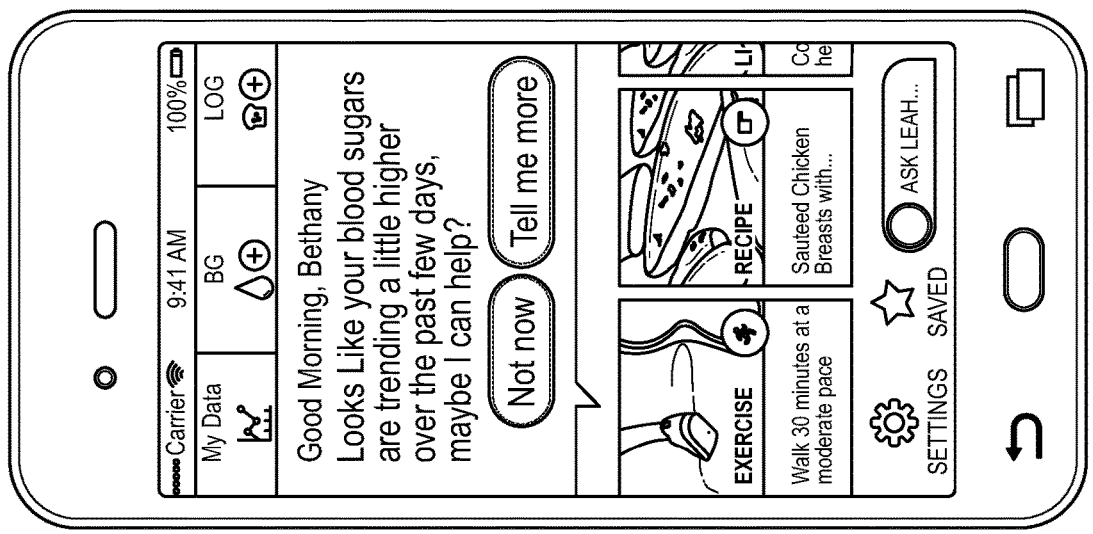
FIG. 7 is an example home screen generated on a user device having an IDM personal application portion of an IDM solution according to an illustrative embodiment.

FIG. 7 illustrates an example IDM personal application 504 home screen (e.g., generated on a touchscreen of a user device 502 that is a smartphone) having icons for convenient selection among options to display "MY DATA," blood glucose or "BG" levels, and a "LOG" of meal data (e.g., to determine amount of ingested carbohydrates). The home screen also has icons for SETTINGS (e.g., to set or change settings associated with the phone app), SAVED data (e.g., saved recipes, BG levels, dose or basal amounts), and a button to select access to an IDM chatbot to commence dialog regarding the patient's disease (e.g., diabetes) to obtain general information about diabetes management. In accordance with an advantageous aspect of the illustrated embodiment, the IDM personal application 504 is programmed to display customized messages and curated content on the user device 502 using, for example, the predictive analysis and machine learning modules 136 and 138 and user data such as, but not limited to, any of the following: dates, times and amounts or levels of BG readings and delivered medication, information related to user's level of activity, indication of mood or general well-being, meal data such as ingested carbohydrates, and history of user interactions with IDM personal application 504 including chatbot inquiries and responses. In the illustrated example, the IDM personal application has analyzed the user's stored data and generated an initial inquiry of "Looks like your blood sugars are trending a little higher over the past few days, maybe I can help?". The screen includes buttons for user options of "TELL ME MORE" and "Not Now." The home screen also provides display buttons for convenient selection of different types of information related to EXERCISE, RECIPE and LIFESTYLE. Selection of any of these three buttons brings the user to different screens such as exercise recommendations, recipes selected based on the user's prior inputs of ingested food or recipe selection or inquiries, and other lifestyle recommendations that can be content retrieved from the content database 150 at the IDM system 500.

The IDM system can include various screens generated on the user device 502 by the IDM personal application 504 to prompt user inputs to facilitate generating future screens that provide the user with a customized experience. For example, the onboarding screens can comprise screens that allow a user to access and manage user settings, to control preferences regarding screen prompts and output formats, to provide user name and other data, to receive screen outputs advising on the degree of user customized experience configured by the user and encouragement to further customize, among other possible onboarding screens.

Figure 8:
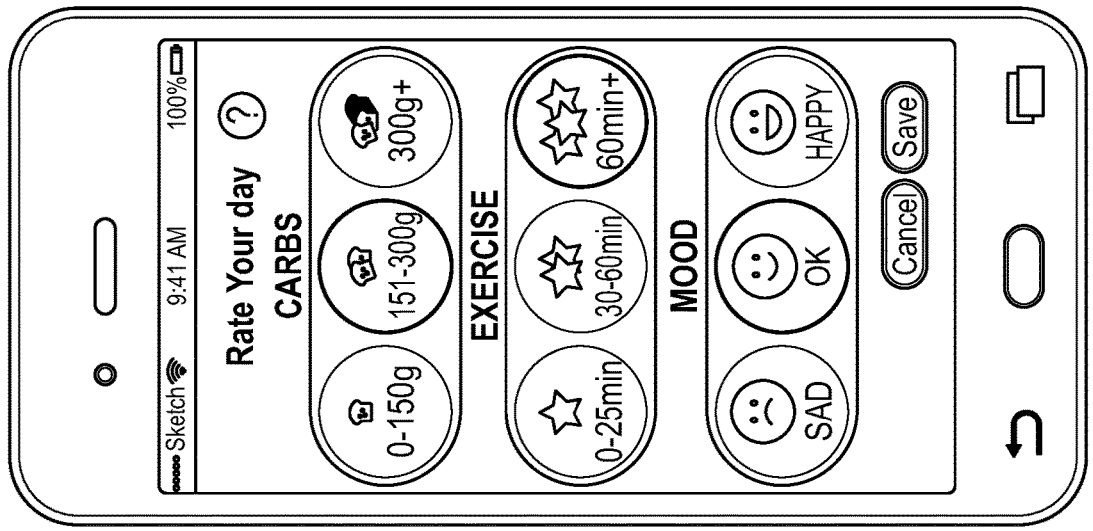
FIGS. 8, 9, 10, and 11 are examples of screens generated on a user device having an IDM personal application portion of an IDM solution for tracking carbohydrate intake, exercise, mood and/or blood glucose values according to an illustrative embodiment.

FIG. 8 is an example "Rate Your Day" screen generated on the user device 502 by the IDM personal application 504 to provide elegant and simple prompts for a user to input information pertaining to three categories of information that are useful to managing diabetes including CARBS, EXERCISE and MOOD. For each of these three categories, there are three ranges of amounts, levels or degrees having respective icons to provide a convenient visual queue for the user. For example, the CARBS category has three different icons representing increasing amounts of bread (e.g., icons representing a bread slice, 2 bread slices and a bread loaf) and correspondingly increasing ranges of grams of carbohydrates. Selecting a button for a respective one of these icons and corresponding carbs range is more convenient than typing an integer number amount. Further, as will be shown and described with reference to FIG. 11, the icon provides a convenient and easy to understand visual display in other displays having a table or chart of icons for that category on one or more days, along with icons from other categories. Similarly, the EXERCISE category has three different icons representing increasing amounts of user activity (e.g., icons representing a star, 2 stars, and 3 stars) and MOOD category has three different icons representing different user mood states (e.g., icons representing a sad face, a smile, and a broader smile) and corresponding moods of the user such as sad, feeling okay and feeling happy. Entering and storing this type of user data is useful to the interactive engine 130 of the system 500 and/or the IDM personal application 504 to determine and generate increasingly customized screens with user information, prompts, inquiries to provide the user with information based on their current state and history of patient data, taking into consideration both quantitative information (e.g., BG readings, delivered medication, carbohydrate intake) and qualitative information (e.g., mood, favorite foods and activities and topics of interest pertaining to lifestyle and disease management).

Figure 9:
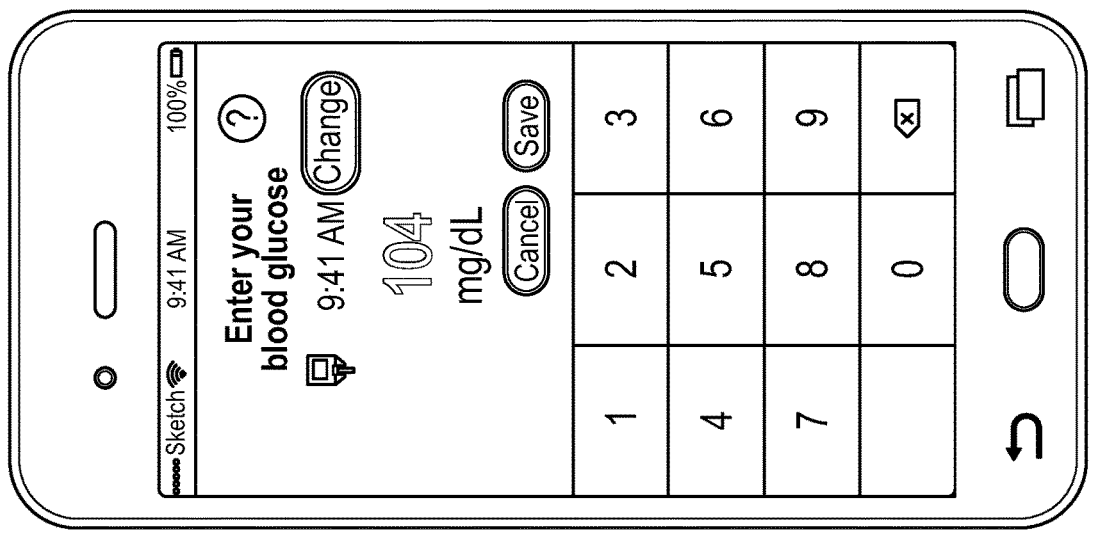

As shown in FIG. 9, the user can manually enter blood glucose level via the IDM personal application 504 on the user device 502. Alternatively, the IDM personal application 504 on the user device 502 is configured with sub-apps to automatically receive data from MDD device(s) 510 and monitoring devices 512 (e.g., via Bluetooth™) and provide the data to IDM system 500 and corresponding private cloud, or obtain MDD or BGM/CGM data or other data from a third party vendor (e.g., via a public cloud 508).

Figure 10:
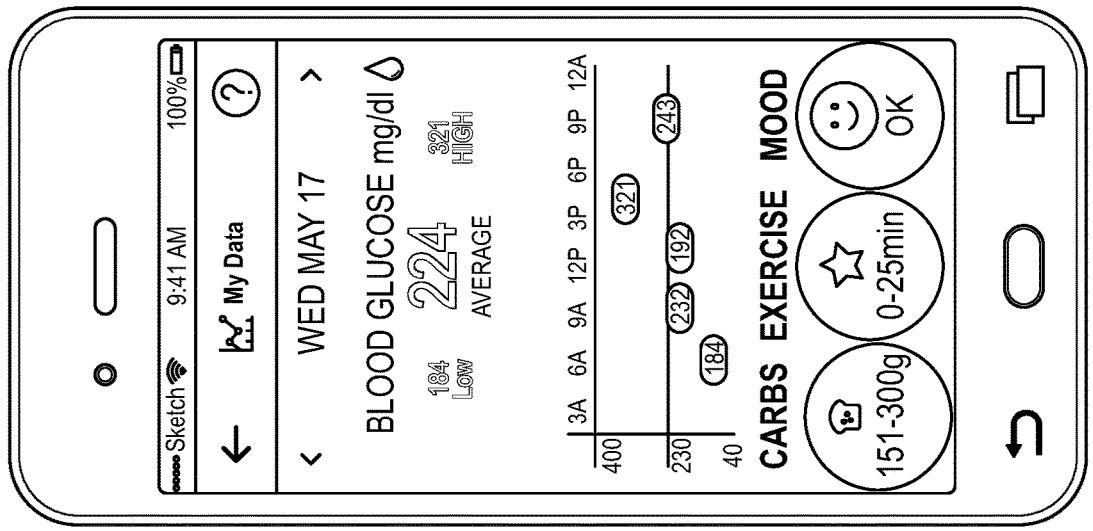
Figure 11:
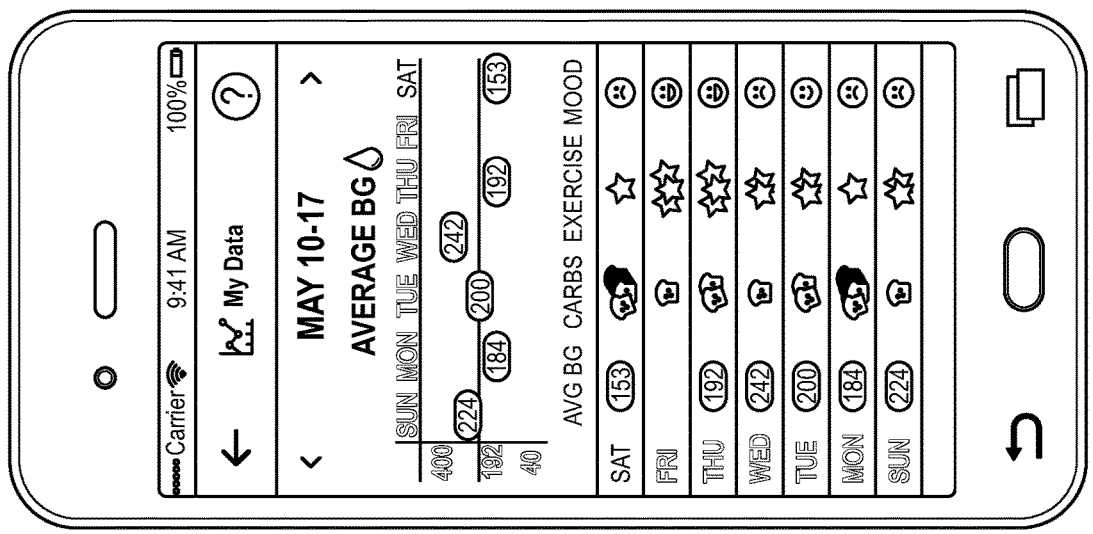
Figure 14:
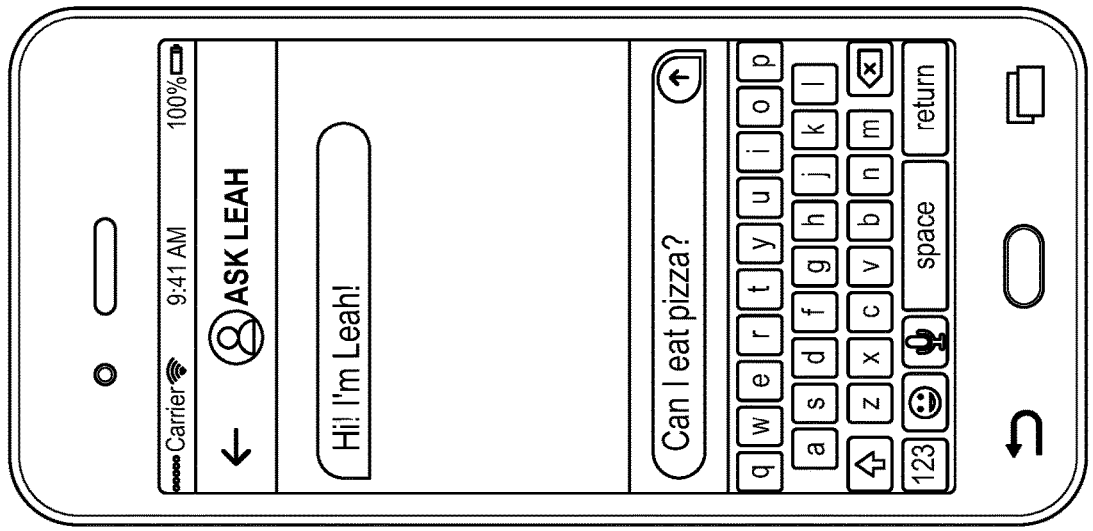
FIGS. 14, 15, 16, 17, and 18 are examples of screens generated on a user device having an IDM personal application portion of an IDM solution illustrating adaptive user interaction according to an illustrative embodiment.

FIGS. 10, 11, and 20 depict illustrative daily and weekly MY DATA screens generated on the user device 502 by the IDM personal application 504. The MY DATA screens employ the "Rate Your Day" icons described with reference to FIG. 8 used for qualifying respective days, and can provide other data such as BG levels on a particular day as shown in the daily MY DATA screen in FIG. 10 or an average BG level on each day of a selected week as shown in the weekly MY DATA screen in FIG. 11. FIG. 20 illustrates a weekly MY Data screen providing a visualization of patient BG level data.

Figure 12:
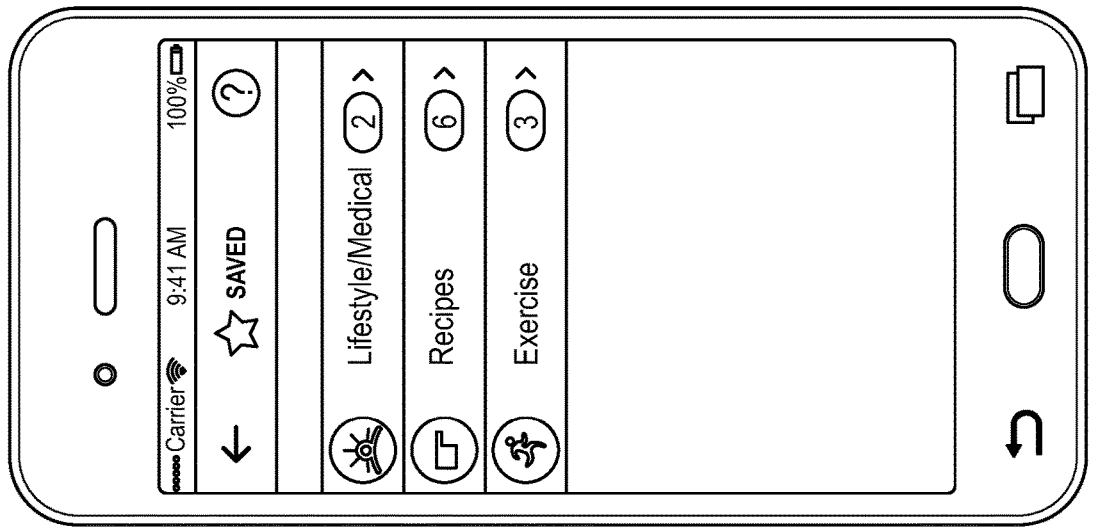
FIGS. 12 and 13 are examples of screens generated on a user device having an IDM personal application portion of an IDM solution for accessing saved lifestyle information according to an illustrative embodiment.
Figure 13:
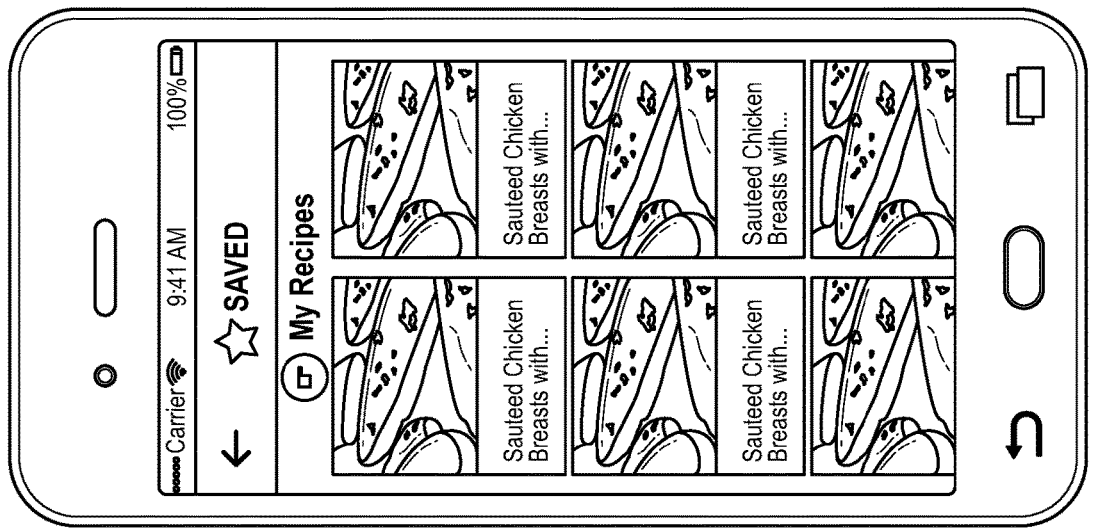

FIGS. 12 and 13 depict illustrative SAVED screens generated on the user device 502 by the IDM personal application 504. FIG. 12 is a table of contents of categories of saved data such as Lifestyle/Medical, Recipes and Exercise including number of articles saved for each category (e.g., 6 recipes). FIG. 13 depicts the MY RECIPES home screen generated when the Recipe category is selected in the SAVED screen of FIG. 12. A user can select any of the buttons corresponding to a recipe to retrieve that recipe.

Figure 16:
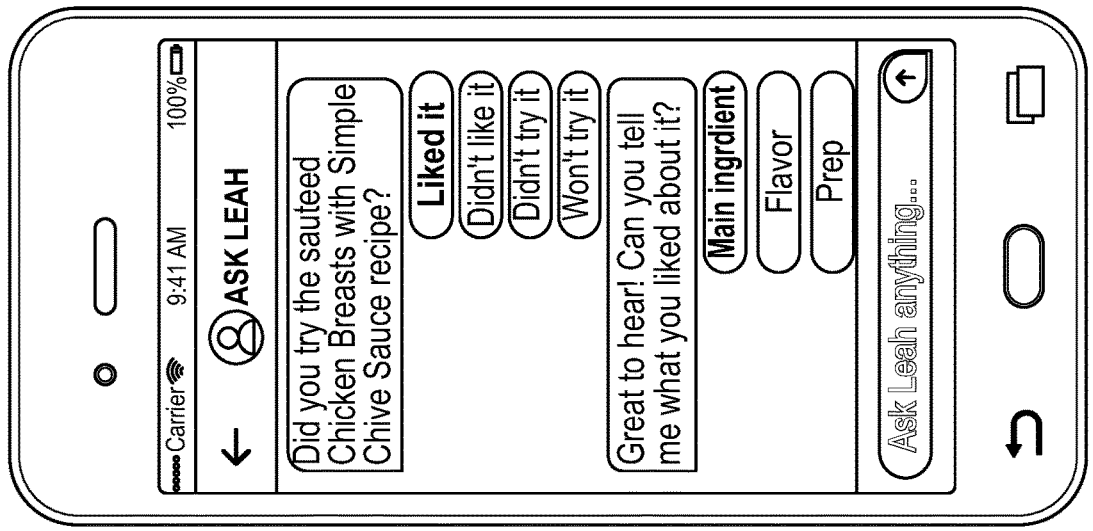
Figure 15:
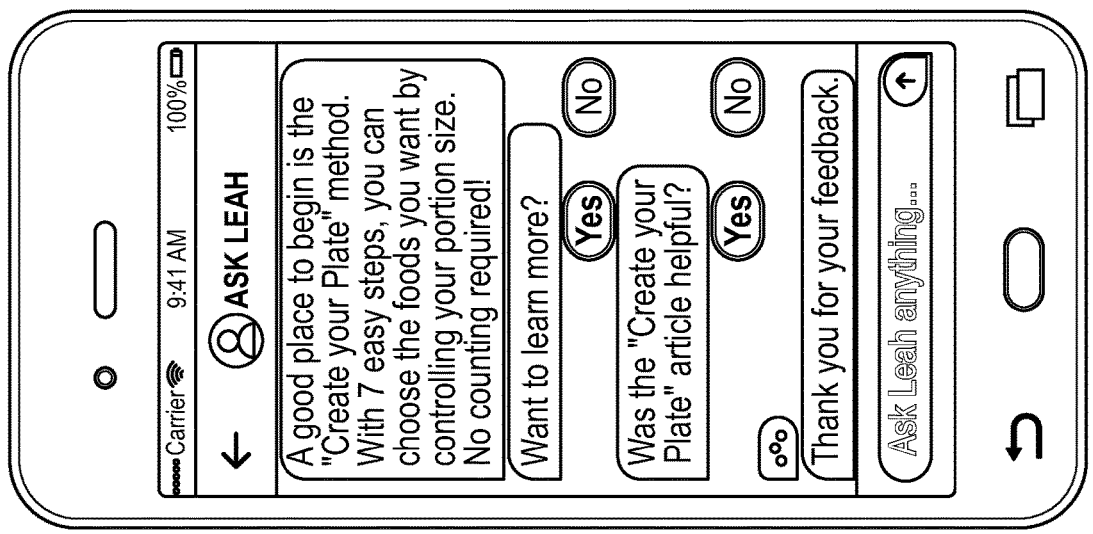
Figure 17:
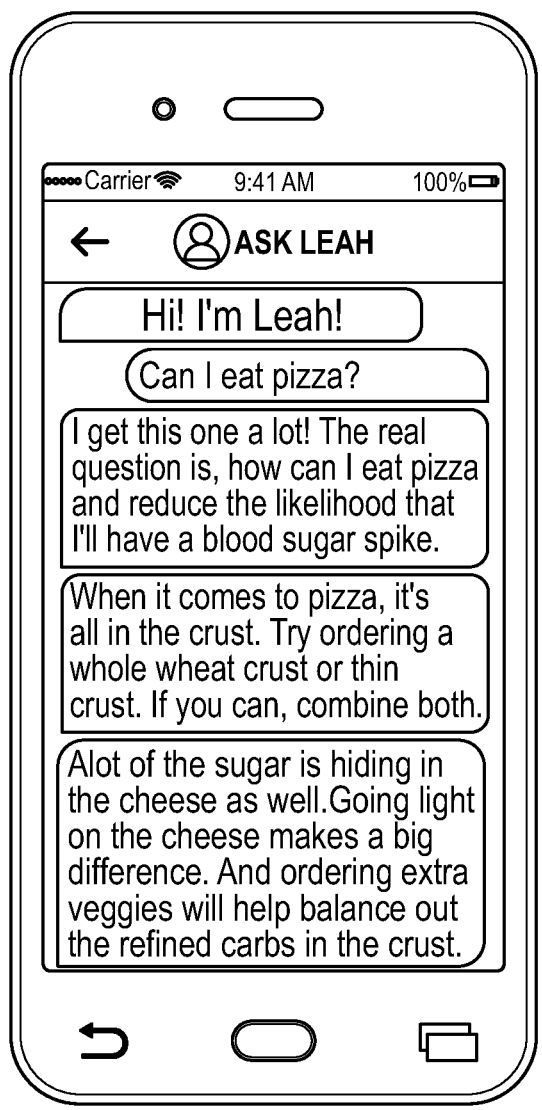
Figure 18:
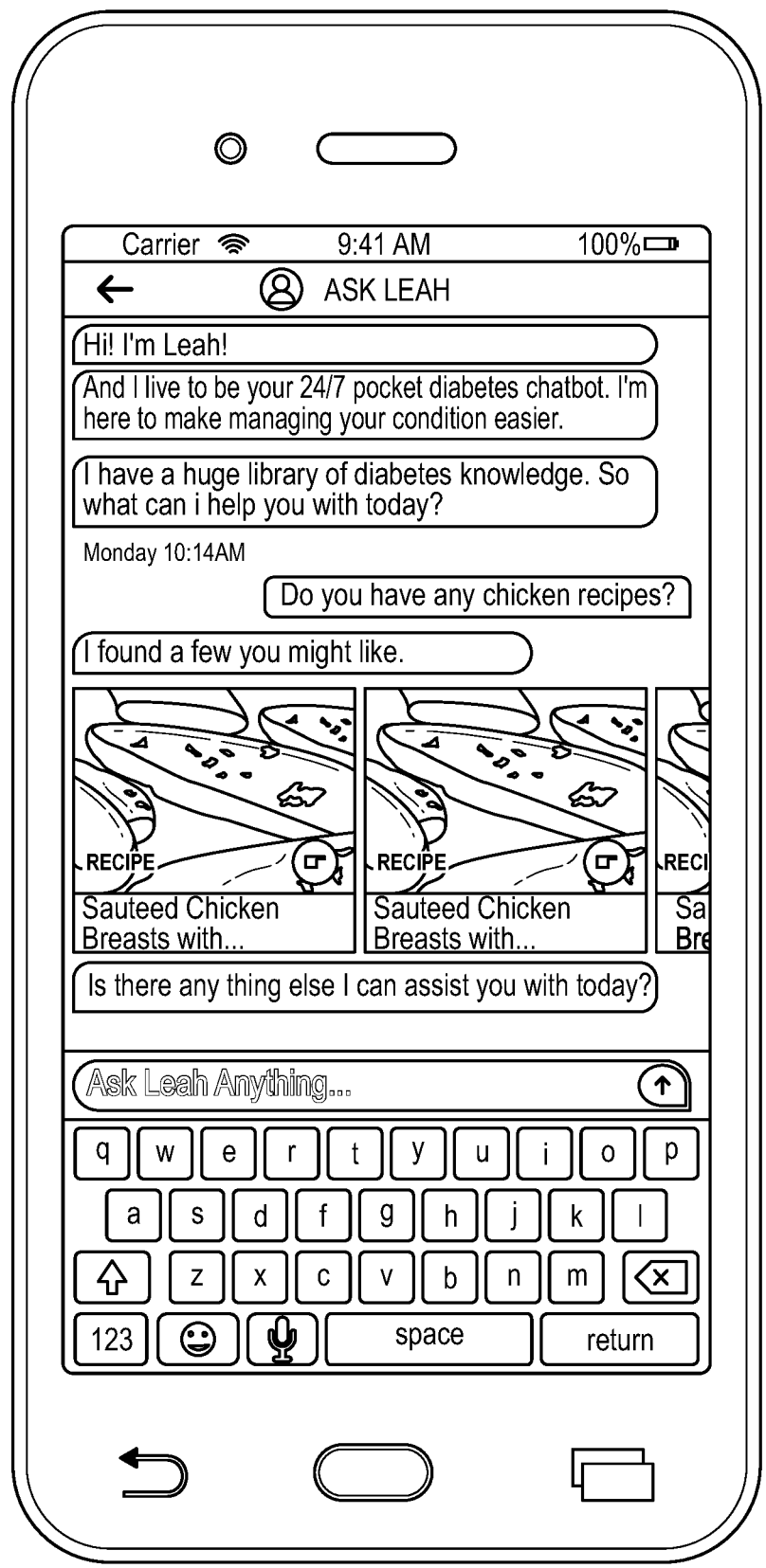

FIGS. 14 through 18 depict illustrative chatbot screens generated on the user device 502 by the IDM personal application 504 and include user inquiries (e.g., "can I eat pizza" in FIG. 14) and chatbot responses in FIG. 15, but also more chatbot inquiries (e.g., prompting a user to rate a recipe and indicate a reason such as "main ingredient" or "Flavor" or "Prep Time" as in FIG. 16) to enable the IDM personal application 504 to provide curated suggested recipes as illustrated in FIG. 18.

The IDM solution described in accordance with illustrative embodiments of the present invention creates conversations to help the patient understand how to more easily manage their condition and drives patient engagement by providing a highly personal and relevant experience that is customized for the patient's type of diabetes, treatment type, food and exercise profile. The structured, real-time, conversations generated using the interactive engine 130 of the IDM system and/or the IDM personal application 504 helps the patient understand the "why", not just the "what" when it comes to their glucose readings being within range or not and what remedial actions they need to take. The IDM solution described herein transforms self-reported tracking data from a merely a number, or what could be an overwhelming amount of patient diabetes data, to an actionable insight and therefore reduces the burdens of care with digital engagement that seamlessly combines unique dose data and blood glucose reading with relevant context. The IDM solution is different from conventional practices of focusing on merely data tracking, whereas the IDM solution advantageously provides personal, relevant content that leads to engagement. The IDM solution generates content that is curated, personalized and progressive and therefore specific for the person's disease state, treatment type and preferences. Further, the user experience provided by the IDM solution grows and evolves with the patient's journey to become increasingly personal and relevant, as well as action-oriented and data-driven. For example, the user action-oriented experience can involve convenient collection of device data (e.g., devices 510 in FIG. 5), digital conversations to identify and promote better health decisions, and leveraging third party and self-reported behaviors to encourage good behavior and gain insight into lapses (e.g., devices 512 in FIG. 5). This IDM system's user experience is data driven in that machine learning is used to adapt the experience to the individual using a machine learning platform that is for specific disease management use cases. Further, the IDM solution employs advanced analytics to power insights to share with the user, behavioral models to support individual paths to improved self-care, and innovative use of artificial intelligence and natural language processing to power conversations about a specific condition with the user.

As a further example, the IDM system's 500 artificial intelligence can provide customer service offerings in a predictive and unique way. For example, the IDM system 500's interactive engine 130 can comprise artificial intelligence-generated conversations with a user (e.g., a patient or care giver) relating to customer service workflow with respect to just about any medical device such as a glucose monitoring device or insulin injection device. In other words, the conversations provide an on-application customer support function that is similar to a user contacting a call center for help with a device, but the conversations adapt and evolve based on the device application 502 and/or the IDM system 500 analyzing user device actions, user inquiries about the device communicated via the IDM system 500 as well as user data (e.g., level of education, stage of disease, treatment regimen and compliance statistics, past user inquiries for assistance, and so on). The interactive engine 130 of the IDM system, in connection with exchanges with the IDM personal application 502, is configured to monitor user initiated inquiries and device inputs and actions and to predict and offer a selected customer service or support function upon detection of the occurrence of selected combination of events (e.g., any combination of device or application status or mode, select range of user data, select words in user-initiated inquiry, select user inputs, and so on). The predictive customer service offering function of the IDM system 500 is advantageous over conventional systems that merely provide user-accessible or pushed tutorials that can be offered via a mobile app, because the predictive customer service offering function of the IDM system 500 monitors for certain user trouble points or events and proactively offers support.

In accordance with another example, the IDM system 500 supports e-commerce such as the acquisition of medical supplies (e.g., disposable supplies for insulin delivery or glucose monitoring) needed for a patient's treatment regimen and other relevant supplies and products (e.g., sugar-free foods). The IDM system 500 is also configured to support other digital service offerings such as artificial-intelligence and machine learning-driven conversations tailored to a user (e.g., based on user data and user device input and output events) to provide seamless and coordinated customer engagement such as between a new product adopter and the HCP, other patients, and/or the product supplier or manufacturer. The IDM system 500 is configured to engage in data mining with respect to a user data (e.g., patient pain or failure points for noncompliance with a treatment regimen or misuse of a product or non-use of a product), as well as optional general patient population data, to predict and provide product offers as well as guidance on injection techniques and specific tutorials or virtual coaching to increase patient treatment regimen compliance and disease management success. The IDM system 500 can also be configured for product cross-selling to gain commercial cooperation between various stakeholders for increased revenue streams and financial incentives among the stakeholders.

Figure 19:
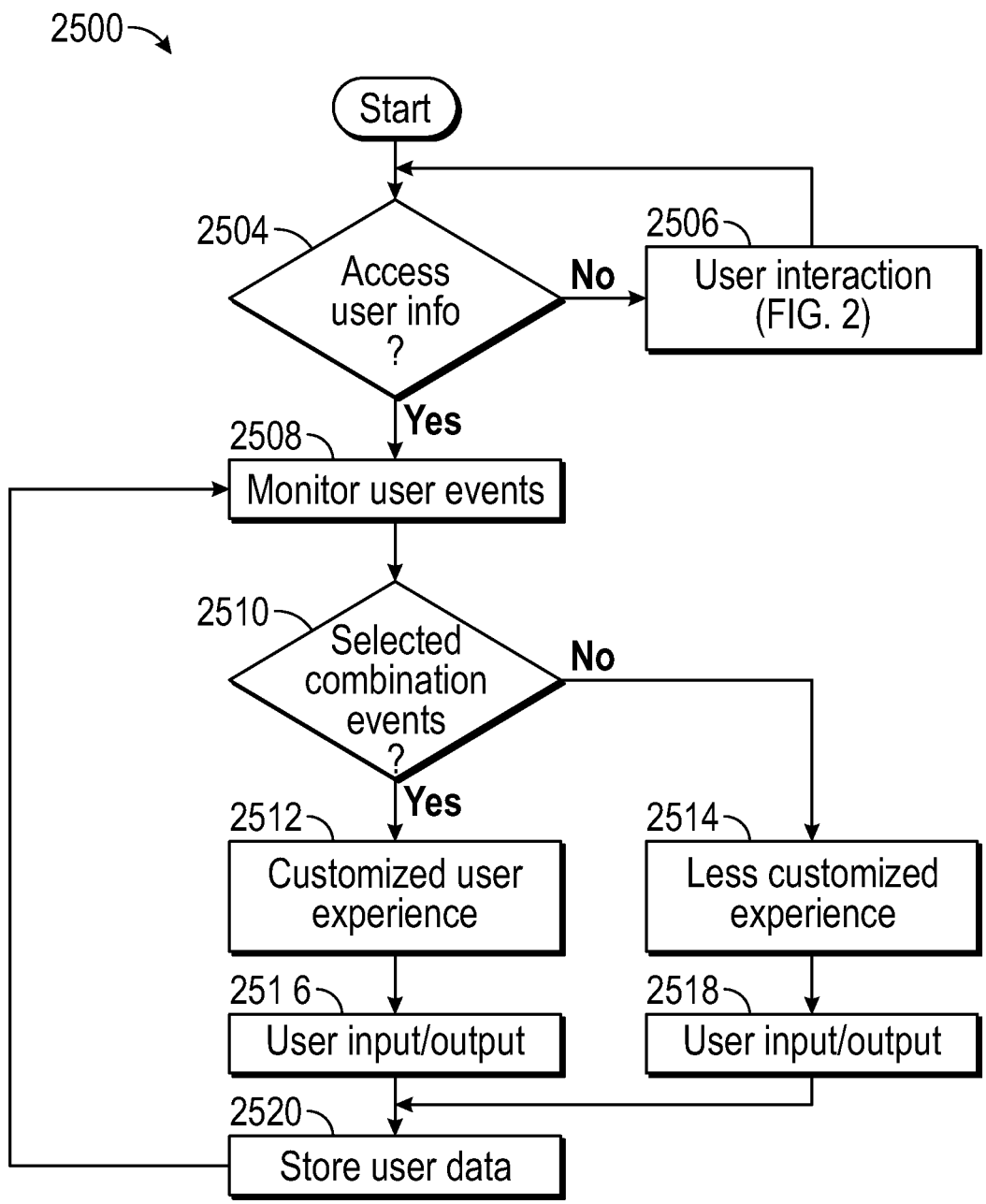
FIG. 19 is a flowchart illustrating an example process for an interactive interface of the IDM system of FIG. 5.

FIG. 19 is a flowchart illustrating an example process 2500 used by the interactive module 130 of the IDM system 500 in interacting with a user (e.g., via the IDM personal application 502). As indicated in block 2502, the IDM system 500 is configured to identify the user and access any stored user information relating to that user (e.g., in a user database 140 of the cloud associated with the IDM system 500 and related to that particular user and/or to users having similar profile information or population data). If information pertaining to the user is available in the cloud for access by the IDM system 500, then the interactive engine 130 commences monitoring user events relative to the device as described (e.g., current or selected date/time range of user data, and histories of user device input and output events) as indicated at block 2508. Alternatively, as indicated at block 2506, the IDM system 500 can commence a process 200 as described above in connection with FIG. 2 and generate an output or general conversation with the user until sufficient user information is available to customize the user experience.

As indicated by block 2510 in FIG. 19, the IDM system 500 is configured to employ artificial intelligence and machine learning and predictive analysis techniques to detect the occurrence(s) of selected combinations of user input/output and user data events to generate a customized experience output (e.g., via the IDM personal application 502 on a user mobile device) as indicated at block 2512. The customized experience can be, for example, a tailored disease management conversation or chatbot string as illustrated in FIGS. 14-18 in addition to specific and customized user behavior recommendations based on user data (e.g., the IDM system 500 operates a chatbot to tell a user "If you are planning on eating pizza tonight, but you indicated you were not feeling well today and yesterday (FIG. 11) and your BG levels have been high this week, then you may want to exercise or reduce your portion and have a lower carb item from the menu."). The customized experience can also be, by way of another example, a predicted offering of a different insulin injection site or technique and related injection product, or a message to confirm automated supply order based on patient inputted (e.g., manually or automated from a device 12,15) delivered insulin amounts to the IDM personal application that, in turn, gets transmitted to the cloud and tracked by the IDM system 500 along with supply replenishment details (preferred brand(s)/supplier(s)/retailer(s), insurance information, and so on).

With continued reference to the process 2500 in FIG. 19, if the selected combination of events in block 2510 does not occur, the IDM 500 can provide other outputs (block 2514) that may be less customized to the user than those described with reference to block 2512. In either case, the user events (e.g., responses and further user inputs and data) in blocks 2516 and 2518 proceeding the outputs in blocks 2512 and 2514, respectively, are stored as indicated at block 2520 to further inform the interactive engine 130 and therefore to further facilitate customization of the user experience.

Example Implementing Systems

Implementations disclosed herein provide systems and methods for IDM systems and related devices or modules. One skilled in the art will recognize that these embodiments may be implemented in hardware, software, firmware, or any combination thereof. Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. A software module may reside in random access memory (RAM), flash memory, ROM, EPROM, EEPROM, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. In other words, the processor and the storage medium may reside in an integrated circuit or be implemented as discrete components.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor. Software or instructions may also be transmitted over a transmission medium. For example, if the software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

In the foregoing description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples.

It is also noted that the examples may be described as a process, which is depicted as a flowchart, a flow diagram, a finite state diagram, a structure diagram, or a block diagram. Although a flowchart may describe the operations as a sequential process, many of the operations can be performed in parallel, or concurrently, and the process can be repeated. In addition, the order of the operations may be re-arranged. A process is terminated when its operations are completed. A process may correspond to a method, a function, a procedure, a subroutine, a subprogram, etc. When a process corresponds to a software function, its termination corresponds to a return of the function to the calling function or the main function.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A method for generating a user interface, the method comprising:
   detecting, by one or more processors of a computing device, whether input regarding a disease of a user satisfies one or more criteria defining a combination of events related to managing the disease, wherein detecting whether input regarding the disease satisfies the one or more criteria comprises:
   determining, by the one or more processors, whether first input regarding one or more user inquiries satisfies at least one first criterion, whether second input regarding medication delivery to the user satisfies at least one second criterion, or whether third input relating to one or more interactions with the user interface satisfies at least one third criterion;

receiving, by the one or more processors, history data comprising a plurality of spoken questions; and applying, by the one or more processors, recognition to the plurality of spoken questions to detect whether the plurality of spoken questions satisfy the one or more criteria defining the combination of events; and in response to detecting that the input satisfies the one or more criteria, identifying, by the one or more processors, one or more user interface options corresponding to the combination of events defined by the one or more criteria, the one or more user interface options related to recommendations to present to the user relating to management of the disease; and outputting, by the one or more processors, for presentation to the user, a customized user interface corresponding to the one or more user interface options by which the user will interact to manage the disease of the user;

wherein the one or more processors comprises a natural language processor.

2. The method of claim 1, further comprising:

generating, by the one or more processors, the user interface to prompt the user for the first input regarding the one or more user inquiries and the second input regarding the medication delivery.

3. The method of claim 1, wherein detecting whether the input regarding the disease of the user satisfies the one or more criteria defining the combination of events further comprises:

generating, by the one or more processors and for display on the user interface, one or more first queries; and in response to determining, by the one or more processors, that the one or more user inquiries do not satisfy the one or more criteria defining the combination of events related to managing the disease of the user, generating, by the one or more processors and for display on the user interface, one or more second queries.

4. The method of claim 1, further comprising:

receiving, by the one or more processors, via the user interface, the first input regarding the one or more user inquiries, the second input regarding the medication delivery to the user, and the third input regarding the one or more interactions with the user interface.

5. The method of claim 1, wherein detecting whether the input regarding the disease of the user satisfies the one or more criteria defining the combination of events further comprises:

receiving, by the one or more processors, history data comprising a device status of the computing device displaying the user interface; and detecting, by the one or more processors, whether the device status satisfies the one or more criteria defining the combination of events.

6. The method of claim 1, wherein detecting whether the input regarding the disease of the user satisfies the one or more criteria defining the combination of events further comprises:

detecting, by the one or more processors, whether select words in the one or more user inquiries satisfy the one or more criteria defining the combination of events.

7. The method of claim 1, wherein detecting whether the input regarding the disease of the user satisfies the one or more criteria defining the combination of events further comprises:

receiving, by the one or more processors, from an insulin injection device, health data comprising timing and dose of an insulin injection; and detecting, by the one or more processors, whether the timing and the dose of the insulin injection satisfy the one or more criteria defining the combination of events.

8. The method of claim 1, wherein detecting whether the input regarding the disease of the user satisfies the one or more criteria defining the combination of events further comprises:

receiving, by the one or more processors, from a diabetes monitoring device, health data comprising blood glucose level measurements and time of the measurements; and detecting, by the one or more processors, whether the blood glucose level measurements and the time of the measurements satisfy the one or more criteria defining the combination of events.

9. The method of claim 1, wherein detecting whether the input regarding the disease of the user satisfies the one or more criteria defining the combination of events further comprises:

receiving, by the one or more processors, from a fitness tracker device, health data comprising user vital measurements relating to heart rate, blood pressure, temperature, blood oxygen level, blood glucose level, physical movements, exercise, sleep pattern, or caloric consumption; and detecting, by the one or more processors, whether the user vital measurements satisfy the one or more criteria defining the combination of events.

10. A system for generating a user interface, the system comprising:

one or more processors coupled to memory, the one or more processors comprising a natural language processor, and the one or more processors configured to:

detect, whether input regarding a disease of a user satisfies one or more criteria defining a combination of events related to managing the disease, wherein detecting whether input regarding the disease satisfies the one or more criteria comprises:

determining whether first input regarding one or more user inquiries satisfies at least one first criterion, whether second input regarding medication delivery to the user satisfies at least one second criterion, or whether third input relating to one or more interactions with the user interface satisfies at least one third criterion; and receiving history data comprising a plurality of spoken questions and applying recognition to the plurality of spoken questions to detect whether the plurality of spoken questions satisfy the one or more criteria defining the combination of events; and in response to detecting that the input satisfies the one or more criteria, identify one or more user interface options corresponding to the combination of events defined by the one or more criteria, the one or more user interface options related to recommendations to present to the user relating to management of the disease; and output, for presentation to the user, a customized user interface corresponding to the one or more user interface options by which the user will interact to manage the disease of the user.

11. The system of claim 10, wherein the one or more processors are further configured to:
generate the user interface to prompt the user for the first input regarding the one or more user inquiries and the second input regarding the medication delivery; and
receive, via the user interface, the first input regarding the one or more user inquiries, the second input regarding the medication delivery to the user, and the third input regarding the one or more interactions with the user interface.

12. The system of claim 10, wherein detecting whether the input regarding the disease of the user satisfies the one or more criteria defining the combination of events further comprises:
generating, for display on the user interface, one or more first queries; and
in response to determining that the one or more user inquiries do not satisfy the one or more criteria defining the combination of events related to managing the disease of the user, generating, for display on the user interface, one or more second queries.

13. The system of claim 10, wherein detecting whether the input regarding the disease of the user satisfies the one or more criteria defining the combination of events further comprises:
receiving history data comprising a device status of a computing device displaying the user interface; and
detecting whether the device status satisfies the one or more criteria defining the combination of events.

14. The system of claim 10, wherein detecting whether the input regarding the disease of the user satisfies the one or more criteria defining the combination of events further comprises:
receiving from an insulin injection device, timing and dose of an insulin injection; and
detecting whether the timing and the dose of the insulin injection satisfy the one or more criteria defining the combination of events.

15. A method for generating a user interface, the method comprising:
detecting, by one or more processors of a computing device, whether input regarding a disease of a user satisfies one or more criteria defining a combination of events related to managing the disease, wherein detecting whether input regarding the disease satisfies the one or more criteria comprises:
determining, by the one or more processors, whether first input regarding one or more user inquiries satisfies at least one first criterion, whether second input regarding medication delivery to the user satisfies at least one second criterion, or whether third input relating to one or more interactions with the user interface satisfies at least one third criterion;
receiving, by the one or more processors, via the user interface, history data comprising one or more selections for carbohydrate intake, exercise, and mood; and
detecting, by the one or more processors, whether the one or more selections for the carbohydrate intake, the exercise, and the mood satisfy the one or more criteria defining the combination of events; and
in response to detecting that the input satisfies the one or more criteria,
identifying, by the one or more processors, one or more user interface options corresponding to the combination of events defined by the one or more criteria, the one or more user interface options related to recommendations to present to the user relating to management of the disease; and
outputting, by the one or more processors, for presentation to the user, a customized user interface corresponding to the one or more user interface options by which the user will interact to manage the disease of the user.

16. A method for generating a user interface, the method comprising:
detecting, by one or more processors of a computing device, whether input regarding a disease of a user satisfies one or more criteria defining a combination of events related to managing the disease, wherein detecting whether input regarding the disease satisfies the one or more criteria comprises determining whether first input regarding one or more user inquiries satisfies at least one first criterion, whether second input regarding medication delivery to the user satisfies at least one second criterion, or whether third input relating to one or more interactions with the user interface satisfies at least one third criterion; and
in response to detecting that the input satisfies the one or more criteria,
identifying, by the one or more processors:
one or more user interface options corresponding to the combination of events defined by the one or more criteria, the one or more user interface options related to recommendations to present to the user relating to management of the disease;
a recommended insulin injection site and a recommended injection product based on the combination of events defined by the one or more criteria; and
the one or more user interface options that are related to the recommended insulin injection site and the recommended injection product; and
outputting, by the one or more processors, for presentation to the user, a customized user interface corresponding to the one or more user interface options by which the user will interact to manage the disease of the user.

17. A system for generating a user interface, the system comprising:
one or more processors coupled to memory, the one or more processors configured to:
detect, whether input regarding a disease of a user satisfies one or more criteria defining a combination of events related to managing the disease, wherein detecting whether input regarding the disease satisfies the one or more criteria comprises determining whether first input regarding one or more user inquiries satisfies at least one first criterion, whether second input regarding medication delivery to the user satisfies at least one second criterion, or whether third input relating to one or more interactions with the user interface satisfies at least one third criterion; and
in response to detecting that the input satisfies the one or more criteria,
identify one or more user interface options corresponding to the combination of events defined by the one or more criteria, the one or more user interface options related to recommendations to present to the user relating to management of the disease;

identify, based on the combination of events defined by the one or more criteria, a recommended insulin injection site and a recommended injection product;

identify the one or more user interface options that are related to the recommended insulin injection site and the recommended injection product; and output, for presentation to the user, a customized user interface corresponding to the one or more user interface options by which the user will interact to manage the disease of the user.

18. A system for generating a user interface, the system comprising:

one or more processors coupled to memory, the one or more processors comprising a natural language processor, and the one or more processors configured to:

detect, whether input regarding a disease of a user satisfies one or more criteria defining a combination of events related to managing the disease, wherein detecting whether input regarding the disease satisfies the one or more criteria comprises:

determining whether first input regarding one or more user inquiries satisfies at least one first criterion, whether second input regarding medication delivery to the user satisfies at least one second criterion, or whether third input relating to one or more interactions with the user interface satisfies at least one third criterion;

receiving, by the one or more processors, via the user interface, history data comprising one or more selections for carbohydrate intake, exercise, and mood; and detecting, by the one or more processors, whether the one or more selections for the carbohydrate intake, the exercise, and the mood satisfy the one or more criteria defining the combination of events; and in response to detecting that the input satisfies the one or more criteria, identify one or more user interface options corresponding to the combination of events defined by the one or more criteria, the one or more user interface options related to recommendations to present to the user relating to management of the disease; and output, for presentation to the user, a customized user interface corresponding to the one or more user interface options by which the user will interact to manage the disease of the user.

* * * * *